(12) United States Patent
Dimitrov et al.

(10) Patent No.: US 9,738,726 B2
(45) Date of Patent: Aug. 22, 2017

(54) HER2-SPECIFIC MONOCLONAL ANTIBODIES AND CONJUGATES THEREOF

(71) Applicant: The United States of America, as represented by the Secretary, Department of Health and Human Services, Washington, DC (US)

(72) Inventors: Dimiter S. Dimitrov, Frederick, MD (US); Zhongyu Zhu, Frederick, MD (US); Pradman K. Qasba, Frederick, MD (US); Boopathy Ramakrishnan, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/897,389

(22) PCT Filed: Jun. 9, 2014

(86) PCT No.: PCT/US2014/041492
§ 371 (c)(1),
(2) Date: Dec. 10, 2015

(87) PCT Pub. No.: WO2014/200891
PCT Pub. Date: Dec. 18, 2014

(65) Prior Publication Data
US 2016/0130359 A1    May 12, 2016

Related U.S. Application Data

(60) Provisional application No. 61/833,732, filed on Jun. 11, 2013.

(51) Int. Cl.
| | | |
|---|---|---|
| *A61K 39/395* | (2006.01) | |
| *C07K 16/32* | (2006.01) | |
| *C07K 16/30* | (2006.01) | |
| *A61K 47/48* | (2006.01) | |
| *G01N 33/574* | (2006.01) | |
| *A61K 39/00* | (2006.01) | |

(52) U.S. Cl.
CPC ........ *C07K 16/32* (2013.01); *A61K 47/48415* (2013.01); *A61K 47/48484* (2013.01); *A61K 47/48569* (2013.01); *A61K 47/48584* (2013.01); *A61K 47/48715* (2013.01); *C07K 16/30* (2013.01); *C07K 16/3015* (2013.01); *G01N 33/57492* (2013.01); *A61K 2039/505* (2013.01); *C07K 2317/21* (2013.01); *C07K 2317/41* (2013.01); *C07K 2317/52* (2013.01); *C07K 2317/55* (2013.01); *C07K 2317/73* (2013.01); *C07K 2317/92* (2013.01); *C07K 2319/00* (2013.01); *G01N 2333/82* (2013.01)

(58) Field of Classification Search
None
See application file for complete search history.

(56) References Cited

U.S. PATENT DOCUMENTS

| | | |
|---|---|---|
| 2006/0084162 A1 | 4/2006 | Qasba et al. |
| 2007/0258986 A1 | 11/2007 | Qasba et al. |

FOREIGN PATENT DOCUMENTS

| | | |
|---|---|---|
| EP | 2 540 745 | 1/2013 |
| WO | WO 03/006509 | 1/2003 |
| WO | WO 2008/019290 | 2/2008 |
| WO | WO 2011/147982 | 12/2011 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Almagro & Fransson, Frontiers in Bioscience 2008; 13:1619-33.*
Carter, Nat Rev Immunol, 2006; 6:343-357.*
Alley et al., "The Pharmacologic Basis for Antibody-Auristatin Conjugate Activity," *J. Pharmacol. Exp. Ther.*, vol. 330:932-938, 2009.
Awwad et al., "Modification of Monoclonal Antibody Carbohydrates by Oxidation, Conjugation, or Deoxymannojirimycin does not Interfere with Antibody Effector Functions," *Cancer Immunol. Immunother.*, vol. 38:23-30, 1994.
Axup et al., "Synthesis of Site-Specific Antibody-Drug Conjugates Using Unnatural Amino Acids," *Proc. Nat. Acad. Sci.*, vol. 109:16101-16106, 2012.
Ballantyne and Dhillon, "Trastuzumab Emtansine: First Global Approval," *Drugs*, pp. 11, 2013.
Bander, "Overview of Antibody-Drug Conjugate Technology for the Clinician," *Clin. Adv. Hemat Oncol.*, vol. 10(8; suppl 10):3-7, 2012.
Bejot et al., "Aminooxy-Functionalized DOTA for Radiolabeling of Oxidized Antibodies: Evaluation of Site-Specific $^{111}$In-Labeled Trastuzumab," *J. Label Compd. Radiopharm.*, vol. 55:346-353, 2012.
Boeggeman et al., "Direct Identification of Nonreducing GlcNAc Residues on N-Glycans of Glycoproteins Using a Novel Chemoenzymatic Method," *Bioconjugate Chem.*, vol. 18:806-814, 2007.

(Continued)

Primary Examiner — Sheela J Huff
(74) Attorney, Agent, or Firm — Klarquist Sparkman, LLP

(57) ABSTRACT

The identification of Her2-specific monoclonal antibody m860 is described. The m860 antibody was identified from a human naïve phage display Fab library by panning against the extracellular domain of human Her2. M860 binds to cell surface-associated Her2 with an affinity comparable to that of trastuzumab (Herceptin®), but binds to a different epitope. Using site-specific glycan engineering, m860 was conjugated to the small molecule drug auristatin F. The antibody-drug conjugate was stable, bound cell-surface expressed Her2 and exhibited potent cell killing of Her2-positive cancer cells, including trastuzumab-resistant breast cancer cells.

32 Claims, 9 Drawing Sheets

(56) References Cited

OTHER PUBLICATIONS

Boeggeman et al., "Site Specific Conjugation of Fluoroprobes to the Remodeled Fc N-Glycans of Monoclonal Antibodies Using Mutant Glycosyltransferases: Application for Cell Surface Antigen Detection," *Bioconjugate Chem.*, vol. 20: 1228-1236, 2009.

Ducry and Stump, "Antibody—Drug Conjugates: Linking Cytotoxic Payloads to Monoclonal Antibodies," *Bioconjugate Chem.*, vol. 21:5-13, 2010.

Krop et al., "A Phase II Study of Trastuzumab Emtansine in Patients with Human Epidermal Growth Factor Receptor 2-Positive Metastatic Breast Cancer who were Previously Treated with Trastuzumab, Lapatinib, an Anthracycline, a Taxane, and Capecitabine," *J. Clin. Oncol.*, vol. 30:3234-3241, 2012.

Life Technologies Corporation, "Universal site-selective labeling of any antibody: A new paradigm," *BioProbes* 69, pp. 1-3, Lifetechnologies.com, 2013.

Pro et al., "Brentuximab Vedotin (SGN-35) in Patients with Relapsed or Refractory Systemic Anaplastic Large-Cell Lymphoma: Results of a Phase II Study," *J. Clin. Oncol.*, vol. 30:2190-2196, 2012.

Qasba et al., "Site-Specific Linking of Biomolecules via Glycan Residues Using Glycosyltransferases," *Biotechnol. Prog.*, vol. 24:520-526, 2008.

Ramakrishnan and Qasba, "Structure-Based Design of β1,4-Galactosyltransferase I (β4Gal-T1) with Equally Efficient N-Acetylgalactosaminyltransferase Activity," *J. Biol. Chem.*, vol. 277:20833-20839, 2002.

Ramakrishnan et al., "Applications of Glycosyltransferases in the Site-specific Conjugation of Biomolecules and Development of a Targeted Drug Delivery System and Contrast Agents for MRI," *Expert Opin. Drug Deliv.*, vol. 5:149-153, 2008.

Scholl et al., "Targeting HER2 in other Tumor Types," *Annals Oncol.*, vol. 12:S81-S87, 2001.

Shen et al., "Conjugation Site Modulates the in vivo Stability and Therapeutic Activity of Antibody-Drug Conjugates," *Nature Biotech.*, vol. 30:184-191, 2012.

Teicher and Doroshow, "The Promise of Antibody-Drug Conjugates," *New Engl. J. Med.*, vol. 367:1847-1848, 2012.

Vaklavas and Forero-Torres, "Safety and Efficacy of Brentuximab Vedotin in Patients with Hodgkin Lymphoma or Systemic Anaplastic Large Cell Lymphoma," *Ther. Adv. Hematol.*, vol. 3:209-225, 2012.

\* cited by examiner

```
                           SEQUENCE LISTING

<160> NUMBER OF SEQ ID NOS: 4

<210> SEQ ID NO 1
  <211> LENGTH: 363
  <212> TYPE: DNA
  <213> ORGANISM: Artificial Sequence
  <220> FEATURE:
  <223> OTHER INFORMATION: Synthetic polynucleotide

<400> SEQUENCE: 1
gaagtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagacagtat    300
agtggctacg acagatacta ctttgactac tggggccagg gaaccctggt caccgtctct    360
tca                                                                  363

<210> SEQ ID NO 2
  <211> LENGTH: 124
  <212> TYPE: PRT
  <213> ORGANISM: Artificial Sequence
  <220> FEATURE:
  <223> OTHER INFORMATION: Synthetic polypeptide

<400> SEQUENCE: 2

Glu Val Gln Leu Val Gln Ser Gly Ala Glu Val Lys Lys Pro Gly Glu
  1               5                   10                  15

Ser Leu Lys Ile Ser Cys Lys Gly Ser Gly Tyr Ser Phe Thr Ser Tyr
                  20                  25                  30

Trp Ile Gly Trp Val Arg Gln Met Pro Gly Lys Gly Leu Glu Trp Met
              35                  40                  45

Gly Ile Ile Tyr Pro Gly Asp Cys Asp Arg Ser Asp Thr Arg Tyr Ser
      50                  55                  60

Pro Ser Phe Gln Gly Gln Val Thr Ile Ser Ala Asp Lys Ser Ile Ser
  65                  70                  75                  80

Thr Ala Tyr Leu Gln Trp Ser Ser Leu Lys Ala Ser Asp Thr Ala Met
                  85                  90                  95

Tyr Tyr Cys Ala Arg Gln Tyr Ser Gly Tyr Asp Arg Tyr Tyr Phe Asp
              100                 105                 110

Tyr Trp Gly Gln Gly Thr Leu Val Thr Val Ser Ser
          115                 120

<210> SEQ ID NO 3
  <211> LENGTH: 333
  <212> TYPE: DNA
  <213> ORGANISM: Artificial Sequence
  <220> FEATURE:
  <223> OTHER INFORMATION: Synthetic polynucleotide

<400> SEQUENCE: 3
cagactgtgg tgacccagga gccatcgttc tcagtgtccc ctggagggac agtcacactc     60
```

```
acttgtggct tgaactctgg ctcagtctca actcgtcact accccagctg gtaccagcag    120
accccaggcc aggctccacg cacgctcatc tacagcacag atattcgctc ttctggggcc    180
cctagtcaca tctctggctc catccttggg aacaaagctg ccctcaccat cacggggcc     240 caggcagatg atgcatctga ttattactgt gcgctctatt tgggtaatgg cattgctgtc    300
ttcggatctg ggaccaaggt caccgtccta ggt                                 333
```

<210> SEQ ID NO 4
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 4

```
Gln Thr Val Val Thr Gln Glu Pro Ser Phe Ser Val Ser Pro Gly Gly
1               5                   10                  15

Thr Val Thr Leu Thr Cys Gly Leu Asn Ser Gly Ser Val Ser Thr Arg
            20                  25                  30

His Tyr Pro Ser Trp Tyr Gln Gln Thr Pro Gly Gln Ala Pro Arg Thr
        35                  40                  45

Leu Ile Tyr Ser Thr Asp Ile Cys Asp Arg Arg Ser Ser Gly Ala Pro
    50                  55                  60

Ser His Ile Ser Gly Ser Ile Leu Gly Asn Lys Ala Ala Leu Thr Ile
65                  70                  75                  80

Thr Gly Ala Gln Ala Asp Asp Ala Ser Asp Tyr Tyr Cys Ala Leu Tyr
                85                  90                  95

Leu Gly Asn Gly Ile Ala Val Phe Gly Ser Gly Thr Lys Val Thr Val
            100                 105                 110

Leu Gly
```

HER2-SPECIFIC MONOCLONAL ANTIBODIES AND CONJUGATES THEREOF

CROSS REFERENCE TO RELATED APPLICATIONS

This is the U.S. National Stage of International Application No. PCT/US2014/04192, filed Jul. 9, 2014, published in English under PCT Article 21(2), which claims the benefit of U.S. Provisional Application No. 61/833,732, filed Jun. 11, 2013, which is herein incorporated by reference in its entirety.

FIELD

This disclosure concerns monoclonal antibodies specific for Her2 and antibody-drug conjugates comprising a Her2-specific antibody, such as for the treatment of Her2-positive cancer.

BACKGROUND

The Her2 (EGFR2, ErbB2) receptor tyrosine kinase is a member of the epidermal growth factor receptor (EGFR) family of transmembrane receptors. Her2 is overexpressed in approximately 20-25% of primary breast cancers (Slamon et al., *Science* 244:707-712, 1989). Overexpression of Her2 has been implicated in the aggressive growth and poor clinical outcome associated with Her2-positive breast tumors (Slamon et al., *Science* 235:177-182, 1987).

Her2-positive breast cancer is commonly treated with trastuzumab (Herceptin®), a humanized IgG1 monoclonal antibody that specifically binds the extracellular domain of human Her2. Trastuzumab kills Her2-expressing cancer cells by mediating antibody-dependent cellular cytotoxicity (ADCC). However, a number of patients treated with trastuzumab do not respond to treatment, or stop responding after a period of time. Furthermore, the majority of patients with tumors that respond to trastuzumab treatment, ultimately progress. Therefore, there is a clinical need to develop further therapies for the treatment of Her2-positive cancer.

A promising form of therapy for cancer involves the use of antibody-drug conjugates (ADCs), which are capable of specifically targeting a cytotoxic agent to malignant cells without causing significant adverse effects on normal tissues (Teicher and Doroshow, *N Engl J Med* 367(19):1847-1848, 2012). ADCs are comprised of a tumor antigen-specific monoclonal antibody conjugated to a cytotoxic drug, such as an anti-microtubule agent (Bander, *Clinical Advances in Hematology & Oncology* 10(8; suppl 10):3-7, 2012). The ideal ADC utilizes an antibody that specifically binds a tumor antigen with reasonable affinity, and exhibits limited or no immunogenicity. The linker should be stable in the circulation so that the cytotoxic agent is not released systemically where it can contact non-target cells. In addition, the linker should maintain attachment of the antibody to the cytotoxic agent until the ADC reaches the tumor and is internalized. Common cytotoxic agents for ADCs include anti-microtubule agents, such as maytansinoids and auristatins (e.g., auristatin E and auristatin F), and pyrrolobenzodiazepines (PDBs) (Bander, *Clinical Advances in Hematology & Oncology* 10(8; suppl 10):3-7, 2012).

SUMMARY

Disclosed herein is a monoclonal antibody that specifically binds the extracellular domain of human Her2 at an epitope different from trastuzumab (Herceptin®). Further disclosed is an antibody-drug conjugate (ADC) comprising the Her2-specific monoclonal antibody m860 conjugated by glycan engineering to a small molecule anti-microtubule agent. The disclosed ADC specifically and potently kills Her2-expressing cancer cells.

Provided herein is an isolated monoclonal antibody that binds, such as specifically binds, Her2. In some embodiments, the monoclonal antibody comprises the CDR sequences of antibody m860 disclosed herein. In some embodiments, the monoclonal antibody comprises the VH domain sequence of m860 (SEQ ID NO: 2) and/or the VL domain sequence of m860 (SEQ ID NO: 4).

Further provided are compositions including the antibodies that bind, for example specifically bind, to Her2, nucleic acid molecules encoding these antibodies, expression vectors comprising the nucleic acid molecules, and isolated host cells that express the nucleic acid molecules. Also provided are conjugates comprising the antibodies disclosed herein and an effector molecule, such as a drug or other therapeutic agent, a toxin, or a detectable label.

The antibodies and compositions provided herein can be used for a variety of purposes, such as for confirming the diagnosis of a cancer that expresses Her2, for example breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma or head and neck carcinoma. Thus, provided herein is a method of confirming the diagnosis of cancer in a subject by contacting a sample from the subject diagnosed with cancer with a monoclonal antibody that binds Her2, and detecting binding of the antibody to the sample. An increase in binding of the antibody to the sample relative to binding of the antibody to a control sample confirms the cancer diagnosis. In some embodiments, the method further includes contacting a second antibody that specifically recognizes the Her2-specific antibody with the sample, and detecting binding of the second antibody.

Similarly, provided herein is a method of detecting a cancer that expresses Her2 in a subject. The method includes contacting a sample from the subject with a monoclonal antibody described herein, and detecting binding of the antibody to the sample. An increase in binding of the antibody to the sample relative to a control sample detects cancer in the subject. In some embodiments, the methods further comprise contacting a second antibody that specifically recognizes the Her2-specific antibody with the sample, and detecting binding of the second antibody.

Further provided is an ADC comprising a drug conjugated to a Her2-specific monoclonal antibody disclosed herein, wherein the drug is conjugated to an N-glycan of a CH2 domain of the antibody.

Also provided herein is a method of treating a subject having a Her2-positive cancer, for example breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma or head and neck carcinoma, by selecting a subject with a cancer that expresses Her2 and administering to the subject a therapeutically effective amount of a monoclonal antibody specific for Her2, or a conjugate (such as an ADC) or composition comprising the antibody. In some examples, the antibody, conjugate or composition is administered in combination with at least one other therapeutic agent for the treatment of a Her2-positive cancer, such as in combination with trastuzumab.

Also provided is a method for inhibiting tumor growth or metastasis in a subject by selecting a subject with a cancer that expresses Her2 and administering to the subject a therapeutically effective amount of an antibody, conjugate (such as an ADC) or composition disclosed herein. In some examples, the antibody, conjugate or composition is administered in combination with at least one other therapeutic agent for the treatment of a Her2-positive cancer, such as in combination with trastuzumab.

The foregoing and other objects, features, and advantages of the invention will become more apparent from the following detailed description, which proceeds with reference to the accompanying figures.

BRIEF DESCRIPTION OF THE DRAWINGS

(FIG. 1A) MALDI-TOF MS analysis of N-glycans released by PNGase F treatment of native m860 IgG1. Shown are the G0F glycoform with a peak at 1485.6 m/z, and the G1F glycoform with a peak at 1647.6 m/z; the G2F glycoform was not detected in this preparation. (FIG. 1B) MALDI-TOF analysis of N-glycans released by PNGase F treatment of β-galactosidase-treated m860 IgG1. Only the G0F glycoform with a peak at 1485.6 m/z was observed after β-galactosidase treatment.

(FIG. 7A) Cytotoxicity assay of Her-2-overexpressing SKRB3 cells. The m860 ADC is slightly more cytotoxic than free drug (nAF) on SKBR3 cells, while the WT m860 IgG1 did not show any cytotoxicity. (FIG. 7B) Cytotoxicity assay of MCF-7 cells, which do not express Her2. The m860 ADC was cytotoxic to MCF-7 cells only at a relatively high concentration, while the free drug with linker alone exhibited significant cytotoxicity to MCF-7 cells. (FIG. 7C) Cytotoxicity assay of JIMT-1 cells. The JIMT-1 cell line, which was isolated from a trastuzumab-resistant patient, had moderate Her2 expression compared to SKBR3. The m860 ADC potently killed JIMT-1 cells, while the WT m860 IgG1 alone had little effect on these cells.

SEQUENCE LISTING

Figure 1A:
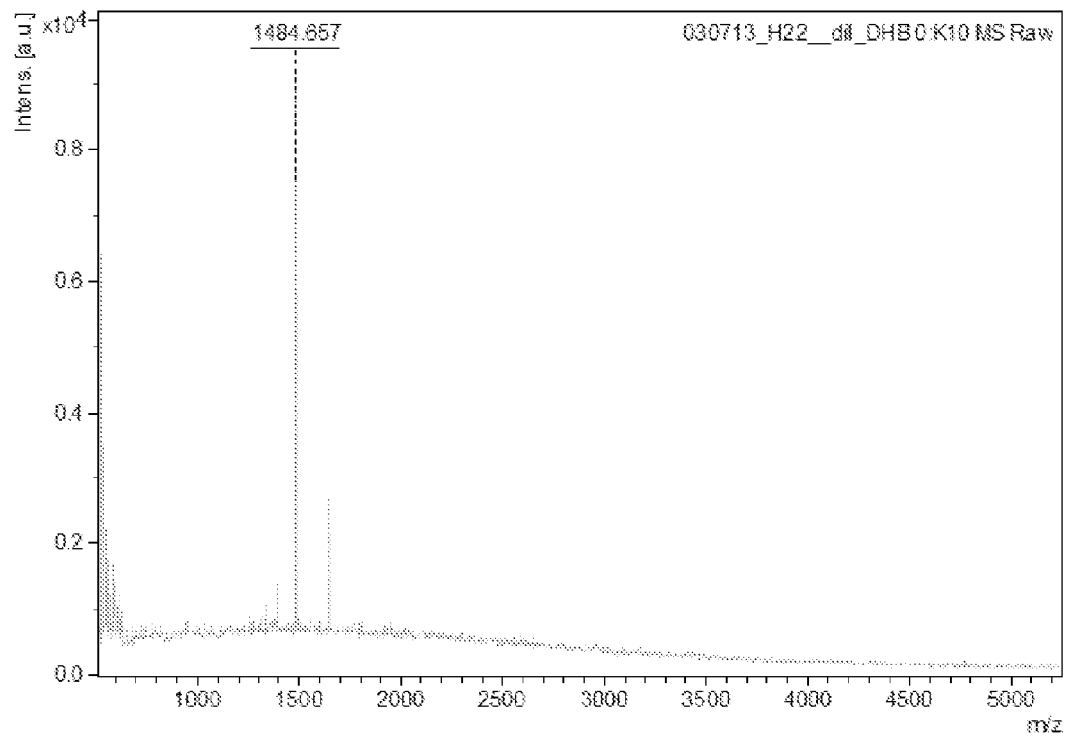
FIGS. 1A-1B: MS analysis of N-glycans after β-galactosidase and sialydase treatment of m860 IgG1.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 7, 2015 3.81 KB, which is incorporated by reference herein. In the accompanying sequence listing:

SEQ ID NO: 1 is the nucleotide sequence of the VH domain of m860.

SEQ ID NO: 2 is the amino acid sequence of the VH domain of m860.

SEQ ID NO: 3 is the nucleotide sequence of the VL domain of m860.

SEQ ID NO: 4 is the amino acid sequence of the VL domain of m860.

DETAILED DESCRIPTION

I. Abbreviations

ADC antibody-drug conjugate
ADCC antibody-dependent cellular cytotoxicity
CAR chimeric antigen receptor
CDR complementarity determining region
CTL cytotoxic T lymphocyte
ECD extracellular domain
EGFR epidermal growth factor receptor
ELISA enzyme-linked immunosorbent assay
MALDI matrix-assisted laser desorption/ionization
MS mass spectrometry
nAF auristatin F with a non-cleavable linker
PE *Pseudomonas* exotoxin
PDB pyrrolobenzodiazepine
TOF time-of-flight
VH variable heavy
VL variable light II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A polypeptide ligand comprising at least a light chain or heavy chain immunoglobulin variable region which recognizes and binds (such as specifically recognizes and specifically binds) an epitope of an antigen, such as Her2, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined according to Kabat et al. (see, Kabat et al., *Sequences of Proteins of Immunological Interest*, U.S. Department of Health and Human Services, 1991) and the ImMunoGeneTics database (IMGT) (see, Lefranc, *Nucleic Acids Res* 29:207-9, 2001). The Kabat database is maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds Her2, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds Her2.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rabbit, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Antibody-drug conjugate (ADC): A molecule that includes an antibody (or antigen-binding fragment of an antibody) conjugated to a drug, such as a cytotoxic agent. ADCs can be used to specifically target a cytotoxic agent to cancer cells through specific binding of the antibody to a tumor antigen expressed on the cell surface. Exemplary drugs for use with ADCs include anti-microtubule agents (such as maytansinoids, auristatin E and auristatin F) and interstrand crosslinking agents (e.g., pyrrolobenzodiazepines; PDBs).

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al. (*Mol. Immunol.*, 16:101-106, 1979). In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigen (such as Her2) is an antibody that binds the antigen with high affinity and does not significantly bind other unrelated antigens.

Breast cancer: A type of cancer that forms in tissues of the breast, usually the ducts (tubes that carry milk to the nipple) and lobules (glands that make milk).

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a Her2-positive cancer, such as breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma, or head and neck carcinoma. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody (or immunoconjugate or ADC) that binds Her2 used in combination with a radioactive or chemical compound.

Conservative variant: "Conservative" amino acid substitutions are those substitutions that do not substantially affect or decrease the affinity of a protein, such as an antibody to Her2. For example, a monoclonal antibody that specifically binds Her2 can include at most about 1, at most about 2, at most about 5, at most about 10, or at most about 15 conservative substitutions and specifically bind a Her2 polypeptide. The term "conservative variant" also includes the use of a substituted amino acid in place of an unsubstituted parent amino acid, provided that antibody specifically binds Her2. Non-conservative substitutions are those that reduce an activity or binding to Her2.

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Conjugate: In the context of the present disclosure, a "conjugate" is an antibody or antibody fragment (such as an antigen-binding fragment) covalently linked to an effector molecule. The effector molecule can be, for example, a drug, toxin, therapeutic agent, detectable label, protein, nucleic acid, lipid, carbohydrate or recombinant virus. An antibody conjugate is often referred to as an "immunoconjugate."

When the conjugate comprises an antibody linked to a drug (e.g., a cytotoxic agent), the conjugate is referred to as an "antibody-drug conjugate" or "ADC."

Contacting: Placement in direct physical association; includes both in solid and liquid form.

Degenerate variant: In the context of the present disclosure, a "degenerate variant" refers to a polynucleotide encoding a Her2 polypeptide or an antibody that binds Her2 that includes a sequence that is degenerate as a result of the genetic code. There are 20 natural amino acids, most of which are specified by more than one codon. Therefore, all degenerate nucleotide sequences are included as long as the amino acid sequence of the Her2 polypeptide or antibody that binds Her2 encoded by the nucleotide sequence is unchanged.

Diagnostic: Identifying the presence or nature of a pathologic condition, such as, but not limited to, cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathological condition, such as cancer or metastasis.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of an antibody conjugate (or immunoconjugate) that is intended to have a desired effect on a cell to which the conjugate is targeted. Effector molecules are also known as effector moieties (EMs), therapeutic agents, or diagnostic agents, or similar terms. Therapeutic agents (or drugs) include such compounds as small molecules, nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the effector molecule can be contained within an encapsulation system, such as a liposome or micelle, which is conjugated to the antibody. Encapsulation shields the effector molecule from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels (e.g., fluorophores, chemiluminescent agents, and enzymes). Radioactive isotopes include $^{35}S$, $^{11}C$, $^{13}N$, $^{15}O$, $^{18}F$, $^{19}F$, $^{99m}Tc$, $^{131}I$, $^{3}H$, $^{14}C$ $^{15}N$, $^{90}Y$, $^{99}Tc$, $^{111}In$ and $^{125}I$.

Epitope: An antigenic determinant. These are particular chemical groups or peptide sequences on a molecule that are antigenic, i.e. that elicit a specific immune response. An antibody specifically binds a particular antigenic epitope on a polypeptide, such as Her2.

Framework region: Amino acid sequences interposed between CDRs. Framework regions include variable light and variable heavy framework regions. The framework regions serve to hold the CDRs in an appropriate orientation for antigen binding.

Her2: A member of the epidermal growth factor (EGF) receptor family of receptor tyrosine kinases. This protein has no ligand binding domain of its own and therefore cannot bind growth factors. However, it does bind tightly to other ligand-bound EGF receptor family members to form a heterodimer, stabilizing ligand binding and enhancing kinase-mediated activation of downstream signaling pathways, such as those involving mitogen-activated protein kinase and phosphatidylinositol-3 kinase. Amplification and/or overexpression of the HER2 gene has been reported in numerous cancers, including breast and ovarian tumors. For example, amplification of the HER2 genes has been reported in approximately 20-25% of primary breast cancers. Her2 is also known as v-erb-b2 erythroblastic leukemia viral oncogene homolog 2, neuro/glioblastoma derived oncogene, epidermal growth factor receptor 2 (EGFR2), ERBB2 and Her-2/neu.

Her2-positive cancer: A cancer that overexpresses Her2. Examples of Her2-positive cancers include, but are not limited to, breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma and head and neck carcinoma.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide, drug or other molecule to a polypeptide, such as an antibody or antibody fragment. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells).

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies and conjugates disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy, such as a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds Her2 or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: An agent that directly or indirectly inhibits the growth of and/or kills cells. Toxins include, for example, *Pseudomonas* exotoxin (PE, such as PE35, PE37, PE38 and PE40), diphtheria toxin (DT), botulinum toxin, abrin, ricin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Her2-Specific Monoclonal Antibodies

Disclosed herein is a monoclonal antibody (m860) that specifically binds the extracellular domain of Her2. The m860 antibody was identified from a human naïve phage display Fab library by panning against the extracellular domain of human Her2. M860 binds to cell surface-associated Her2 with an affinity comparable to that of trastuzumab (Herceptin®), but binds to a different epitope. Using site-specific glycan engineering, m860 was conjugated to the small molecule drug auristatin F. The antibody-drug conjugate was stable, bound cell-surface expressed Her2 and exhibited potent cell killing of Her2-positive cancer cells, including trastuzumab-resistant breast cancer cells. The nucleotide and amino acid sequences of the VH and VL domains of m860 are shown below. The CDRs (as determined by IMGT) are indicated with bold underline.

M860 VH nucleotide sequence
(SEQ ID NO: 1)
gaagtgcagctggtgcagtctggagcagaggtgaaaaagcccggggagt ctctgaagatctcctgtaagggttctggatacagctttaccagctactg gatcggctgggtgcgccagatgcccgggaaaggcctggagtggatgggg atcatctatcctggtgactctgataccagatacagcccgtccttccaag gccaggtcaccatctcagccgacaagtccatcagcaccgcctacctgca gtggagcagcctgaaggcctcggacaccgccatgtattactgtgcgaga cagtatagtggctacgacagatactactttgactactggggccagggaa ccctggtcaccgtctcttca M860 VH protein sequence
(SEQ ID NO: 2)
EVQLVQSGAEVKKPGESLKISCKGSGYSFTSYWIGWVRQMPGKGLEWMG

IIYPGDSDTRYSPSFQGQVTISADKSISTAYLQWSSLKASDTAMYYCAR

QYSGYDRYYFDYWGQGTLVTVSS

H-CDR1=residues 26-33 of SEQ ID NO: 2
H-CDR2=residues 50-58 of SEQ ID NO: 2
H-CDR3=residues 97-110 of SEQ ID NO: 2

M860 VL nucleotide sequence
(SEQ ID NO: 3)
cagactgtggtgacccaggagccatcgttctcagtgtccctggaggg acagtcacactcacttgtggcttgaactctggctcagtctcaactcgt cactacccagctggtaccagcagacccaggccaggctccacgcacg ctcatctacagcacagatattcgctcttctggggcccctagtcacatc tctggctccatccttgggaacaaagctgccctcaccatcacgggggcc caggcagatgatgcatctgattattactgtgcgctctatttgggtaat ggcattgctgtcttcggatctgggaccaaggtcaccgtcctaggt M860 VL protein sequence
(SEQ ID NO: 4)
QTVVTQEPSFSVSPGGTVTLTCGLNSGSVSTRHYPSWYQQTPGQAPRT

LIYSTDIRSSGAPSHISGSILGNKAALTITGAQADDASDYYCALYLGN

GIAVFGSGTKVTVLG

L-CDR1=residues 23-34 of SEQ ID NO: 4
L-CDR2=residues 52-54 of SEQ ID NO: 4
L-CDR3=residues 91-100 of SEQ ID NO: 4

Provided herein are isolated monoclonal antibodies that bind (for example, specifically bind) Her2, such as cell-surface or soluble Her2. In some embodiments, the VH domain of the antibody comprises at least a portion of the amino acid sequence set forth herein as SEQ ID NO: 2, such as one or more (such as all three) CDR sequences from SEQ ID NO: 2. In some embodiments, the VL domain of the antibody comprises at least a portion of the amino acid sequence set forth herein as SEQ ID NO: 4, such as one or more (such as all three) CDR sequences from SEQ ID NO: 4.

In some embodiments, the VH domain of the antibody that binds Her2 comprises amino acid residues 26-33, 50-58 and 97-110 of SEQ ID NO: 2 and/or the VL domain of the antibody comprises amino acid residues 23-34, 52-54 and 91-100 of SEQ ID NO: 4. In some examples, the amino acid sequence of the VH domain is at least 80%, at least 85%, at least 90%, at least 95%, at least 96%, at least 97%, at least 98% or at least 99% identical to SEQ ID NO: 2; and/or the amino acid sequence of the VL domain is at least 80%, at least 85%, at least 90%, at least 95%, at least 96%, at least 97%, at least 98% or at least 99% identical to SEQ ID NO: 4. In particular examples, the VH domain of the antibody comprises SEQ ID NO: 2 and/or the VL domain of the antibody comprises SEQ ID NO: 4.

Also provided are isolated monoclonal antibodies that bind, such as specifically bind, Her2, wherein the antibody comprises a VH domain comprising the amino acid sequence of SEQ ID NO: 2; and/or the VL domain comprises the amino acid sequence of SEQ ID NO: 4.

In some embodiments, the antibody is a Fab fragment, a Fab' fragment, a F(ab)'₂ fragment, a single chain variable fragment (scFv), or a disulfide stabilized variable fragment (dsFv). In other embodiments, the antibody is an immunoglobulin molecule. In particular examples, the antibody is an IgG, such as an $IgG_1$.

Further provided herein are isolated conjugates comprising a Her2-specific monoclonal antibody and an effector molecule. In some embodiments, the effector molecule is a drug, such as a small molecule drug. In particular examples, the drug is auristatin F. In other embodiments, the effector molecule is a toxin, such as *Pseudomonas* exotoxin or a variant thereof. In yet other embodiments, the effector molecule is a detectable label. In some examples, the detectable label is a fluorescence, enzymatic, or radioactive label.

Also provided by the present disclosure are compositions comprising a therapeutically effective amount of a disclosed Her2 antibody and a pharmaceutically acceptable carrier. Further provided are compositions comprising a therapeutically effective amount of a conjugate disclosed herein and a pharmaceutically acceptable carrier.

Further provided herein are isolated nucleic acid molecules encoding the disclosed monoclonal antibodies or conjugates. In some embodiments, the nucleotide sequence encoding the VH domain of the monoclonal antibody comprises at least a portion of SEQ ID NO: 1, such as a portion of SEQ ID NO: 1 encoding one or more CDRs. In some embodiments, the nucleotide sequence encoding the VL domain of the monoclonal antibody comprises at least a portion of SEQ ID NO: 3, such as a portion of SEQ ID NO: 3 encoding one or more CDRs. In some examples, the nucleotide sequence encoding the VH domain of the monoclonal antibody comprises SEQ ID NO: 1 and/or the nucleotide sequence encoding the VL domain of the monoclonal antibody comprises SEQ ID NO: 3.

In some examples, the isolated nucleic acid molecule is operably linked to a promoter.

Also provided are expression vectors comprising the isolated nucleic acid molecules disclosed herein. Isolated host cells comprising the nucleic acid molecules or vectors are also provided herein.

IV. Antibodies and Antibody Fragments

The monoclonal antibodies disclosed herein can be of any isotype. The monoclonal antibody can be, for example, an IgM or an IgG antibody, such as $IgG_1$ or an $IgG_2$. The class of an antibody that specifically binds Her2 can be switched with another (for example, IgG can be switched to IgM), according to well-known procedures. Class switching can also be used to convert one IgG subclass to another, such as from $IgG_1$ to $IgG_2$.

Antibody fragments are also encompassed by the present disclosure, such as single-domain antibodies (e.g., VH domain antibodies), Fab, F(ab')$_2$, and Fv. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV2), defined as a dimer of a scFV (also known as a "miniantibody"); and (7) VH single-domain antibody, an antibody fragment consisting of a heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and/or the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

V. Antibody Conjugates

The disclosed monoclonal antibodies specific for Her2 can be conjugated via any means known in the art to an effector molecule, such as a drug, therapeutic agent, diagnostic reagent or other effector moiety, to generate a conjugate (also referred to as an "immunoconjugate").

A. Drugs and Therapeutic Agents

A therapeutic agent is an agent with a particular biological activity directed against a particular target molecule or a cell bearing a target molecule. Drugs or therapeutic agents include, for example, small molecules, toxins, cytotoxic agents, nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

In some embodiments, the conjugate is an immunotoxin, which comprises a covalent linkage of an antibody (or antibody fragment) to a cytotoxin, such as native or modified *Pseudomonas* exotoxin or diphtheria toxin. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022).

In some examples, the PE is a variant that is resistant to lysosomal degradation, such as PE-LR (Weldon et al., *Blood* 113(16):3792-3800, 2009; PCT Publication No. WO 2009/032954. In other examples, the PE is a variant designated PE-LR/6X (PCT Publication No. WO 2011/032022). In other examples, the PE variant is PE with reduced immunogenicity. In yet other examples, the PE is a variant designated PE-LR/8M (see PCT Publication No. WO 2011/032022).

In some embodiments, the effector molecule linked to the Her2-specific antibody can be an encapsulation system, such as a liposome or micelle that contains a diagnostic agent, therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985).

The choice of a particular therapeutic agent or other effector moiety depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

B. Diagnostic and Detection Moieties

An antibody that binds (for example specifically binds) Her2 or a fragment thereof can be labeled with a detectable moiety. Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorophores, chemiluminescent agents, and enzymes.

Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) or yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect Her2 by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

C. Conjugation Methods

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids. Conjugation can also be achieved by glycan engineering, which is discussed below in section VI.

In some circumstances, it is desirable to free the effector molecule from the antibody when the conjugate has reached its target site. Therefore, in these circumstances, conjugates will comprise linkages that are cleavable in the vicinity of the target site. Cleavage of the linker to release the effector molecule from the antibody may be prompted by enzymatic activity or conditions to which the conjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies, one skilled in the art will be able to determine a suitable method for attaching a given agent to an antibody or other polypeptide.

VI. Antibody-Drug Conjugates by Site-Specific Glycan Engineering

Antibody-drug conjugates (ADCs) are compounds comprised of a tumor antigen-specific antibody and a drug, typically a cytotoxic agent, such as an anti-microtubule agent. Because ADCs are capable of specifically targeting cancer cells, the cytotoxic agent can be much more potent than agents used for standard chemotherapy. The most common cytotoxic drugs currently used with ADCs have an IC$_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. Currently, most ADCs use a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

Described herein is the use of a method for site-specific and stable conjugation of a drug to a monoclonal antibody via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Utilization of the site-specific glycan engineering conjugation method is described herein in Examples 1 and 2. Use of this site-specific antibody-drug conjugation method minimizes the potential undesirable modification of the peptide backbone of the antibody, thereby improving efficacy and safety profile with lower immunogenicity. This method also has the potential to increase stability of the ADC and increase half-life of the ADC in vivo. It is believed that this method will lower the non-specific binding of the ADC to non-target cells and tissues in vivo, and reduce off-target toxicity.

Provided herein is an ADC comprising a drug (such as a cytotoxic agent) conjugated to a monoclonal antibody that binds (such as specifically binds) Her2, wherein the drug is conjugated to an N-glycan of a CH2 domain of the antibody. In some embodiments, the VH domain of the antibody comprises amino acid residues 26-33, 50-58 and 97-110 of SEQ ID NO: 2 and the VL domain of the antibody comprises amino acid residues 23-34, 52-54 and 91-100 of SEQ ID NO: 4. In some examples, the amino acid sequence of the VH domain is at least 80%, at least 85%, at least 90%, at least 95%, at least 96%, at least 97%, at least 98% or at least 99% identical to SEQ ID NO: 2; and/or the amino acid sequence of the VL domain is at least 80%, at least 85%, at least 90%, at least 95%, at least 96%, at least 97%, at least 98% or at least 99% identical to SEQ ID NO: 4. In particular examples, the VH domain of the antibody comprises SEQ ID NO: 2 and/or the VL domain of the antibody comprises SEQ ID NO: 4.

In some embodiments of the ADC, the drug is a small molecule. In some examples, the drug is an anti-microtubule and/or anti-mitotic agent, or any cytotoxic agent suitable for mediating killing of tumor cells. Exemplary cytotoxic agents include, but are not limited to, an auristatin, such as auristatin F or auristatin E, a maytansinoid, or a PDB. In particular examples herein, the small molecule drug is auristatin F. In one non-limiting embodiment, the drug is auristatin F comprising a non-cleavable linker, for example a non-cleavable linker at the C-terminus of auristatin F.

In some embodiments of the ADC, the antibody to drug ratio is 1:4. In other embodiments, the antibody to drug ratio is 1:2.

The ADCs disclosed herein can be used for the treatment of a Her2-positive cancer alone or in combination with another therapeutic agent and/or in combination with any standard therapy for the treatment of cancer (such as surgical resection of the tumor, chemotherapy or radiation therapy). Since the m860 ADC disclosed herein binds to an epitope of Her2 that is different from the epitope to which trastuzumab binds, the Her2-specific ADCs disclosed herein can be used in combination with trastuzumab (Herceptin®).

VII. Compositions and Methods of Use

Compositions are provided that include one or more of the disclosed antibodies that bind (for example specifically bind) Her2 in a carrier. Compositions comprising antibody conjugates (such as immunotoxins and ADCs) are also provided. The compositions can be prepared in unit dosage forms for administration to a subject. The amount and timing of administration are at the discretion of the treating clinician to achieve the desired outcome. The antibody can be formulated for systemic or local (such as intra-tumor) administration. In one example, the antibody is formulated for parenteral administration, such as intravenous administration.

The compositions for administration can include a solution of the antibody or conjugate dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody or conjugate in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

ADCs are typically administered by intravenous infusion. Doses of ADCs vary, but generally range between about 0.5 mg/kg to 5 mg/kg, such as about 1 mg/kg, 2 mg/kg, 3 mg/kg, 4 mg/kg or 5 mg/kg. ADCs are administered according to a dosing schedule determined by a medical practitioner. In some examples, the ADC is administered weekly, every two weeks, every three weeks or every four weeks.

Antibodies may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN® in 1997. Antibodies and conjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Deliv-*

*ery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

A. Therapeutic Methods

The antibodies and conjugates disclosed herein can be administered to kill tumor cells, to slow or inhibit the growth of tumor cells or to inhibit the metastasis of tumor cells. In these applications, a therapeutically effective amount of an antibody or conjugate (such as an ADC) is administered to a subject in an amount sufficient to inhibit growth, replication or metastasis of cancer cells, or to inhibit a sign or a symptom of the cancer. Suitable subjects may include those diagnosed with a cancer that expresses Her2, such as, but not limited to, breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma and head and neck carcinoma.

In one non-limiting embodiment, provided herein is a method of treating a subject with cancer by selecting a subject having a cancer that expresses Her2 and administering to the subject a therapeutically effective amount of an antibody or conjugate disclosed herein.

Also provided herein is a method of inhibiting tumor growth or metastasis by selecting a subject having a cancer that expresses Her2 and administering to the subject a therapeutically effective amount of an antibody or conjugate disclosed herein.

A therapeutically effective amount of a Her2-specific antibody or conjugate will depend upon the severity of the disease and the general state of the patient's health. A therapeutically effective amount of the antibody is that which provides either subjective relief of a symptom(s) or an objectively identifiable improvement as noted by the clinician or other qualified observer.

Administration of the antibodies and conjugates (or compositions thereof) disclosed herein can also be accompanied by administration of other anti-cancer agents or therapeutic treatments (such as surgical resection of a tumor). Any suitable anti-cancer agent can be administered in combination with the antibodies and conjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells. In one embodiment, an antibody or conjugate disclosed herein is administered in combination with trastuzumab.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin®, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting expression of Her2 in vitro or in vivo. In some cases, Her2 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

One embodiment provides a method of determining if a subject has cancer by contacting a sample from the subject with a monoclonal antibody (or conjugate) disclosed herein; and detecting binding of the antibody to the sample. An increase in binding of the antibody to the sample as compared to binding of the antibody to a control sample identifies the subject as having cancer.

Another embodiment provides a method of confirming a diagnosis of cancer in a subject by contacting a sample from a subject diagnosed with cancer with a monoclonal antibody (or conjugate) disclosed herein; and detecting binding of the antibody to the sample. An increase in binding of the antibody to the sample as compared to binding of the antibody to a control sample confirms the diagnosis of cancer in the subject.

In some examples of the disclosed methods, the monoclonal antibody is directly labeled.

In some examples, the methods further include contacting a second antibody that specifically binds the monoclonal antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma or head and neck carcinoma, or any other type of cancer that expresses Her2.

In some examples, the control sample is a sample from a subject without cancer. In particular examples, the sample is a blood or tissue sample.

In some cases, the antibody that binds (for example specifically binds) Her2 is directly labeled with a detectable label. In another embodiment, the antibody that binds (for example, specifically binds) Her2 (the first antibody) is unlabeled and a second antibody or other molecule that can bind the antibody that specifically binds Her2 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium, and non-limiting exemplary radioactive labels include $^{125}I$, $^{131}I$, $^{35}S$ or $^{3}H$.

In an alternative embodiment, Her2 can be assayed in a biological sample by a competition immunoassay utilizing Her2 standards labeled with a detectable substance and an unlabeled antibody that specifically binds Her2. In this assay, the biological sample, the labeled Her2 standards and the antibody that specifically bind Her2 are combined and the amount of labeled Her2 standard bound to the unlabeled antibody is determined. The amount of Her2 in the biological sample is inversely proportional to the amount of labeled Her2 standard bound to the antibody that specifically binds Her2.

The immunoassays and method disclosed herein can be used for a number of purposes. In one embodiment, the antibody that specifically binds Her2 may be used to detect the production of Her2 in cells in cell culture. In another embodiment, the antibody can be used to detect the amount of Her2 in a biological sample, such as a tissue sample, or a blood or serum sample. In some examples, the Her2 is cell-surface Her2. In other examples, the Her2 is soluble Her2, such as Her2 in a cell culture supernatant or soluble Her2 (e.g. the extracellular domain of Her2) in a body fluid sample, such as a blood or serum sample).

In one embodiment, a kit is provided for detecting Her2 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble Her2 protein or fragment (e.g. the extracellular domain of Her2). Kits for detecting a polypeptide will typically comprise a monoclonal antibody that specifically binds Her2, such as an antibody disclosed herein. In some embodiments, an antibody fragment, such as a scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds Her2. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting Her2 in a biological sample generally includes the steps of contacting the biological sample with an antibody which specifically reacts, under immunologically reactive conditions, to a Her2 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind Her2, as disclosed herein, can be used in these assays. Thus, the antibodies can be used in a conventional immunoassay, including, without limitation, an ELISA, an RIA, FACS, tissue immunohistochemistry, Western blot or immunoprecipitation.

C. Engineered Cytotoxic T Lymphocytes (CTLs)

The disclosed monoclonal antibodies can also be used to produce CTLs engineered to express chimeric antigen receptors (CARs; also known as chimeric T cell receptors, artificial T cell receptors or chimeric immunoreceptors). Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv. Several different endodomains have been used to generate CARs. For example, the endodomain can consist of a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, the monoclonal antibodies disclosed herein can be used to engineer CTLs that express a CAR containing an antigen-binding fragment of a Her2-specific antibody, thereby targeting the engineered CTLs to Her2-expressing tumor cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expressed the target antigen.

Accordingly, provided herein are CARs comprising a Her2-specific antibody binding fragment, such as a scFv. Also provided are isolated nucleic acid molecules and vectors encoding the CARs, and host cells, such as CTLs, comprising the nucleic acid molecules or vectors. CTLs expressing CARs comprised of a Her2-specific antibody binding fragment can be used for the treatment of cancers that express Her2, such as breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma or head and neck carcinoma. Thus, provided herein are methods of treating a subject with cancer by selecting a subject having a cancer that expresses Her2, and administering to the subject a therapeutically effective amount of the CTLs expressing the Her2-targeted CARs.

D. Bispecific Antibodies

Bispecific antibodies are recombinant proteins comprised of antigen-binding fragments of two different monoclonal antibodies. Thus, bispecific antibodies bind two different antigens. Bispecific antibodies can be used for cancer immunotherapy by simultaneously targeting both CTLs (such as a CTL receptor component such as CD3) and a tumor antigen. The Her2-specific monoclonal antibodies disclosed herein can be used to generate bispecific antibodies that target both Her2 and CTLs, thereby providing a means to treat Her2-expressing cancers.

Provided herein are bispecific monoclonal antibodies comprising a Her2-specific monoclonal antibody, or antigen-binding fragment thereof. In some embodiments, the bispecific monoclonal antibody further comprises a monoclonal antibody, or antigen-binding fragment thereof, that specifically binds a component of the T cell receptor, such as CD3. Also provided are isolated nucleic acid molecules and vectors encoding the bispecific antibodies, and host cells comprising the nucleic acid molecules or vectors. Bispecific antibodies comprising a Her2-specific antibody, or antigen-binding fragment thereof, can be used for the treatment of cancers that express Her2, such as breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma or head and neck carcinoma. Thus, provided herein are methods of treating a subject with cancer by selecting a subject having a cancer that expresses Her2, and administering to the subject a therapeutically effective amount of the Her2-targeting bispecific antibody.

The following examples are provided to illustrate certain particular features and/or embodiments. These examples should not be construed to limit the disclosure to the particular features or embodiments described.

EXAMPLES

Example 1: Antibody-Drug Conjugate Comprising a Her2-Specific Antibody

This example describes the identification of a Her2-specific monoclonal antibody (m860) from a phage library and the development of a Her2-specific antibody-drug conjugate (ADC) by site-specific glycan engineering. The Her2-specific ADC exhibits potent cell killing of Her2-expressing cancer cells.

Materials and Methods

Reagents

Recombinant β1,4 galactosidase from *Streptococcus pneumoniae* was from Calbiochem (San Diego, Calif.). Peptide N-glycoside F (PNGase F) was from New England Biolabs (Ipswich, Mass.). Microcon Ultracel YM-50 centrifugation devices came from Millipore Corporation, (Bedford, Mass.). Protein A-Sepharose 4B Conjugate was from Invitrogen (Eugene, Oreg.). UDP-C2-keto-Gal was synthesized by Allichem LLC (Baltimore, Md.). Auristatin F with noncleavable linker (nAF) attached at C-terminus (Axup et al., *Proc Natl Acad Sci USA* 109:16101-16106, 2012), which was synthesized by Concortis Biosystems.

Synthesis of UDP-C2-Keto-Galactose and Auristatin F with Non-Cleavable Linker Attached at C-Terminus UDP-C2-Keto-Galactose (structure shown below) was synthesized at Allichem LLC:

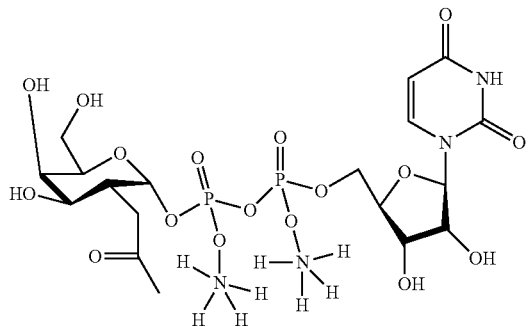

Auristatin F with a non-cleavable linker attached at the C-terminus (nAF) was synthesized at Concortis Biosystems. The molecule structure of nAF is:

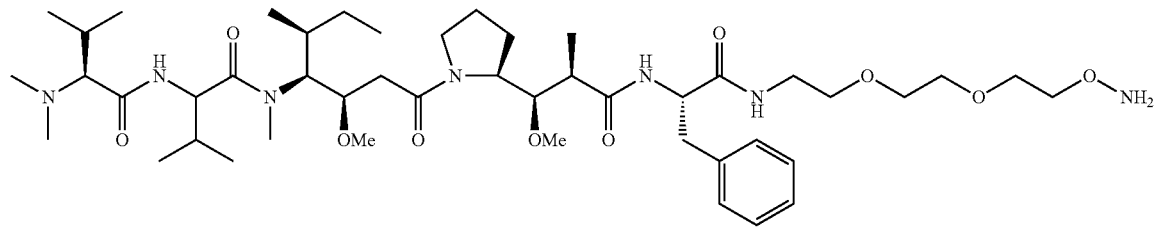 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCON)OC)N(C)C(=O)C(NC(=O)[C@H](C(C)C)N(C)C)C(C)C]

Selection of Her2 Specific Antibody from a Phage Display Human Naïve Fab Library A naïve human Fab phage display library (a total of about 1010 members), constructed from peripheral blood B cells of 10 healthy donors, was used for selection of Fabs against Her2-ECD-Fc fusion protein (R&D systems) conjugated to magnetic beads (DYNABEADS™ M-270 epoxy, Invitrogen). Amplified libraries of 1012 phage-displayed Fabs were incubated with 5, 3 and 1 g of Her2-ECD-Fc in a 500-μl volume for 2 hours at room temperature during the first, second and third rounds of biopanning, respectively. After each round of incubation, the beads were washed 5 times for the first round and 15 times for the later rounds with phosphate-buffered saline containing 0.05% Tween 20 (PBST) to remove nonspecifically bound phage. The bead-bound phage were mixed with TG1 cells for 1 hour at 37° C., and the phage was amplified from the infected cells and used in the next round of biopanning. After the third round of biopanning, 190 clones were randomly picked and monoclonal phage was prepared and used for phage ELISA screening to identify the positive binders. Five unique clones were identified from the screening, of which m860 gave the highest binding activity and was selected for further characterization. The nucleotide and amino acid sequences of the m860 VH and VL domains are set forth herein as SEQ ID NOs: 1-4.

Conversion of Fab to IgG1 and IgG1 Expression and Purification

The m860 Fab heavy and light chains were amplified and recloned in the PDR12 vector for whole immunoglobulin G1 (IgG1) expression. The resulting construct was transfected, and the IgG1 was expressed using the FreeStyle 293 expression kit following the protocol from the manufacturer (Invitrogen, Carlsbad, Calif.). The IgG1 was purified from the culture medium with a protein G column (Sigma-Aldrich, St. Louis, Mo.). A CHO cell based stable clone was also made and used for the production of the IgG1.

Degalactosylation of m860 IgG1

M860 IgG1 in 25 mM Tris-HCl buffer pH8.0 at 5 mg/mL was incubated with 200 mU of recombinant *Streptococcus pneumoniae* β1,4-galactosidase for 24 hours at 37° C. Removal of terminal galactose residues was confirmed by analysis of the N-glycans released after PNGase F treatment by MALDI/TOF spectrometry. Approximately 3 g of WT m860 IgG1 and degalactosylated m860 IgG1 were treated with PNGase F (2500 units) at 37° C. for 16 hours in PBS before being analyzed by MALDI/TOF mass spectrometry. Degalactosylated m860 IgG1 molecules were then purified by protein A affinity chromatography and dialyzed into 25 mM Tris-HCl buffer pH8.0.

Transfer of C-2 Keto Galactose from its UDP-Derivative to Free GlcNAc Residues on m860 IgG1 Using the Mutant Enzyme β1,4Gal-T1-Y289L Ten mg of degalactosylated m860 IgG1 was incubated with 2 mM UDP-C2 keto-Gal and 3 mg of the mutant β1,4Gal-T1-Y289L in 5 ml final incubation mixture containing 10 mM $MnCl_2$ and 25 mM Tris-HCl (pH 8.0). Reactions were incubated at 37° C. for 48 hours. The keto-labeled m860 IgG1 was purified on protein A column and subsequently dialyzed into 100 mM acetate buffer (pH 4.5).

Conjugation of nAF to Keto-Labeled m860 IgG1 Through Oxime Ligation

M860 IgG1 was conjugated at 5 mg/mL and 1 mM nAF in 100 mM acetate buffer pH 4.5 at 37° C. for 3 days. Conjugated antibody was purified on a protein A column to remove the free drug, and dialyzed into PBS for cell-based function analysis. Conjugated glycan was released from the ADC by PNGase F treatment and analyzed using MALDI/TOF mass spectrometry.

Matrix-Assisted Laser Desorption/Ionization Mass Spectrometry (MALDI MS)

Typically 1-2 μL of sample was mixed with an equal volume of 2,5-dihydrobenzoic acid (DHB) matrix solution prepared by dissolving 100 mg of DHB (Sigma Chemicals) in 1 mL of a 1:1 solution of water and acetonitrile. In some instances, a matrix solution of a mixture of DHB/DMA (N,N-dimethylaniline) was used, which was prepared by adding 30 μL of distilled DMA to the DHB matrix. Mixtures were spotted onto a stainless steel plate after mixing the samples and matrix solutions (1 μL each). The samples were dried by evaporation at room temperature. A hybrid triple-quad time-of-flight (QqTOF) mass spectrometer (QSTAR XL, Applied Biosystems, Inc., Framingham, Mass.) was configured for matrix-assisted laser desorption/ionization (MALDI). Mass spectrometry (MS) data was obtained using a laser intensity=21 000 μj, pulse rate=20 Hz, collision gas (CAD)=3 (high purity argon, Airgas, Inc., Frederick, Md.), focusing potential (FP)=35 V, declustering potential (DP)=0 V, declustering potential 2 (DP2)=20 V, and ion energy (IE1)=0.8 V. All samples were analyzed in the positive mode with a 3 minute accumulation time over an m/z range of 150-5000 amu.

High-Resolution Mass Spectrometry Measurement of the Molecular Weights of the Light Chains and Heavy Chains of m860 IgG1 and m860ADC Antibodies (m860 IgG1 and m860 ADC) in PBS were incubated with 10 mM DTT at 65° C. for 10 minutes to break the light chain and heavy chain of the whole antibody before mass spectrometry analysis. Mass spectrometry data were acquired on an Agilent 6520 Accurate-Mass Q-TOF LC/MS System (Agilent Technologies, Inc., Santa Clara, Calif.) equipped with a dual electro-spray source, operated in the positive-ion mode. Separation was performed on Zorbax 300SB-C3 Poroshell column (2.1 mm×75 mm; particle size 5 μm). The analytes were eluted at a flow rate of 1 ml/min with a 1 to 90% organic gradient over 5 minutes and holding organic for 1 minute. Both mobile phases, water and acetonitrile, contained 0.1% formic acid. The instrument was used in a full-scan TOF mode. MS source parameters were set with a capillary voltage of 4 kV, the fragmentor voltage of 220 V and skimmer 65 V. The gas temperature was 350° C., drying gas flow 12 l/min and nebulizer pressure 55 psig. Data were acquired at high resolution (3,200 m/z), 4 GHz. TOF-MS mass spectra were recorded across the range 100-3,200 m/z. To maintain mass accuracy during the run time, an internal mass calibration sample was infused continuously during the LC/MS runs. Data acquisition was performed using Mass Hunter Workstation (version B.02.00). For data analysis and deconvolution of mass spectra, Mass Hunter Qualitative Analysis software (version B.03.01) with Bioconfirm Workflow was used.

Flow Cytometry Analysis to Compare the Binding Activity of m860 IgG1 and m860 ADC to Her2 on SKBR3 Cells SKBR3 breast cancer cells, which overexpress Her2, were detached in cell dissociation buffer and rinsed in PBS. Aliquots of cells were incubated with primary antibodies m860 and m860 ADC at indicated concentrations in 250 μL PBSA for 1 hour on ice. Unbound antibodies were washed away with PBSA. The secondary antibody, goat anti-human IgG conjugated with PE (Sigma), was diluted at 1:100 and incubated with cells on ice for 30 minutes. Cells were washed and resuspended in PBSA buffer for flow cytometry analysis on FACSCalibur (Becton Dickinson).

Size Exclusion Chromatography

ADC m860 was purified and analyzed using a Superdex200 10/300 GL column (GE Healthcare, Piscataway, N.J.) calibrated with protein molecular mass standards of 14-kDa RNase A, 25-kDa chymotrypsin, 44-kDa ovalbumin, 67-kDa albumin, 158-kDa aldolase, 232-kDa catalase, 440-kDa ferritin, and 669-kDa thyroglobulin. Purified m860ADC in phosphate-buffered saline (PBS) was loaded onto the pre-equilibrated column and eluted with PBS at 0.5 ml/min.

Comparison of the Binding Affinities of m860 and m860 ADC to FcγRIII (CD16) and FcγRI (CD64) Measured by Surface Plasmon Resonance Interactions between the antibodies and CD16 and CD64 were analyzed by surface plasmon resonance technology using a Biacore™ X100 instrument (GE healthcare). CD16 or CD64 was covalently immobilized onto a sensor chip (CM5) using carbodiimide coupling chemistry. A control reference surface was prepared for nonspecific binding and refractive index changes. For analysis of the kinetics of interactions, varying concentrations of antibodies were injected at flow rate of 30 μL/min using running buffer containing 10 mmol/L HEPES, 150 mmol/L NaCl, 3 mmol/L EDTA, and 0.05% Surfactant P-20 (pH=7.4). The association and dissociation phase data were fitted simultaneously to a 1:1 model by using BIAevaluation 3.2. All the experiments were done at 25° C.

In Vitro Cytotoxicity Assay

SKBR3, MCF-7 and JIMT-1 cells were cultured and assayed in DMEM (Life Technologies) with 10% (vol/vol) FBS (Gibco), 100 IU/mL penicillin, and 100 g/mL streptomycin (Life Technologies). For the cytotoxicity assays, the cancer cell lines were plated in 96-well plates at ~1,000 cells in 70 μL per well in culture medium and incubated overnight at 37° C. and 5% $CO_2$. Drugs (m860 IgG1, m860 ADC and free drug nAF) were filtered (0.22 μm; Millipore) and 30 μl of serially diluted drugs in culture medium were added into the wells in duplicate and incubated at 37° C. for 72 hours. Colorimetric reagent (Promega) was then added to each well. After a 3-hour incubation at 37° C., the absorbance at 490 nm was measured, and IC50 was determined by GraphPad Prism.

Results

Identification, Expression and Characterization of IgG1 m860

Five different Fabs with unique sequences were identified after three rounds of panning against a recombinant Her2 protein ectodomain. All Fabs showed specific binding activity to tumor cell surface expressed Her2 with various affinities and none of the Fabs competed with Herceptin. One of the antibodies, m860, was converted into full size human IgG1. The IgG1 m860 was produced from a CHO based stable clone and was used for the ADC generation.

Figure 1B:
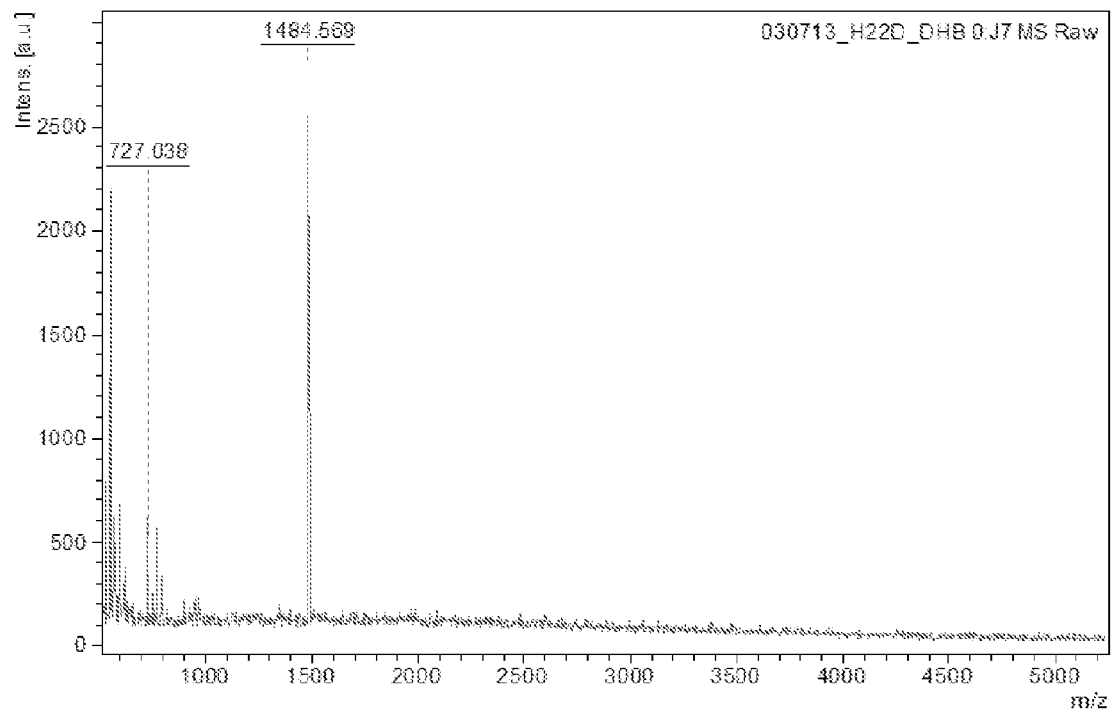

Confirmation of Degalactosylation of m860 IgG1 by MS Analysis of Released Glycan MS analysis of N-glycans after β-galactosidase and sialydase treatment of m860 IgG1 was performed to confirm that m860 was degalactosylated. FIG. 1A shows the results of MALDI-TOF MS analysis of N-glycans released by PNGase F treatment of native m860 IgG1. The G0F and G1F glycoforms produced a peak at 1485.6 m/z and 1647.6 m/z, respectively; the G2F glycoform was not detected. Shown in FIG. 1B are the results of MALDI-TOF analysis of N-glycans released by PNGase F treatment of β-galactosidase-treated m860 IgG1. Only the G0F glycoform, with a peak at 1485.6 m/z, was observed after β-galactosidase treatment.

Figure 2:
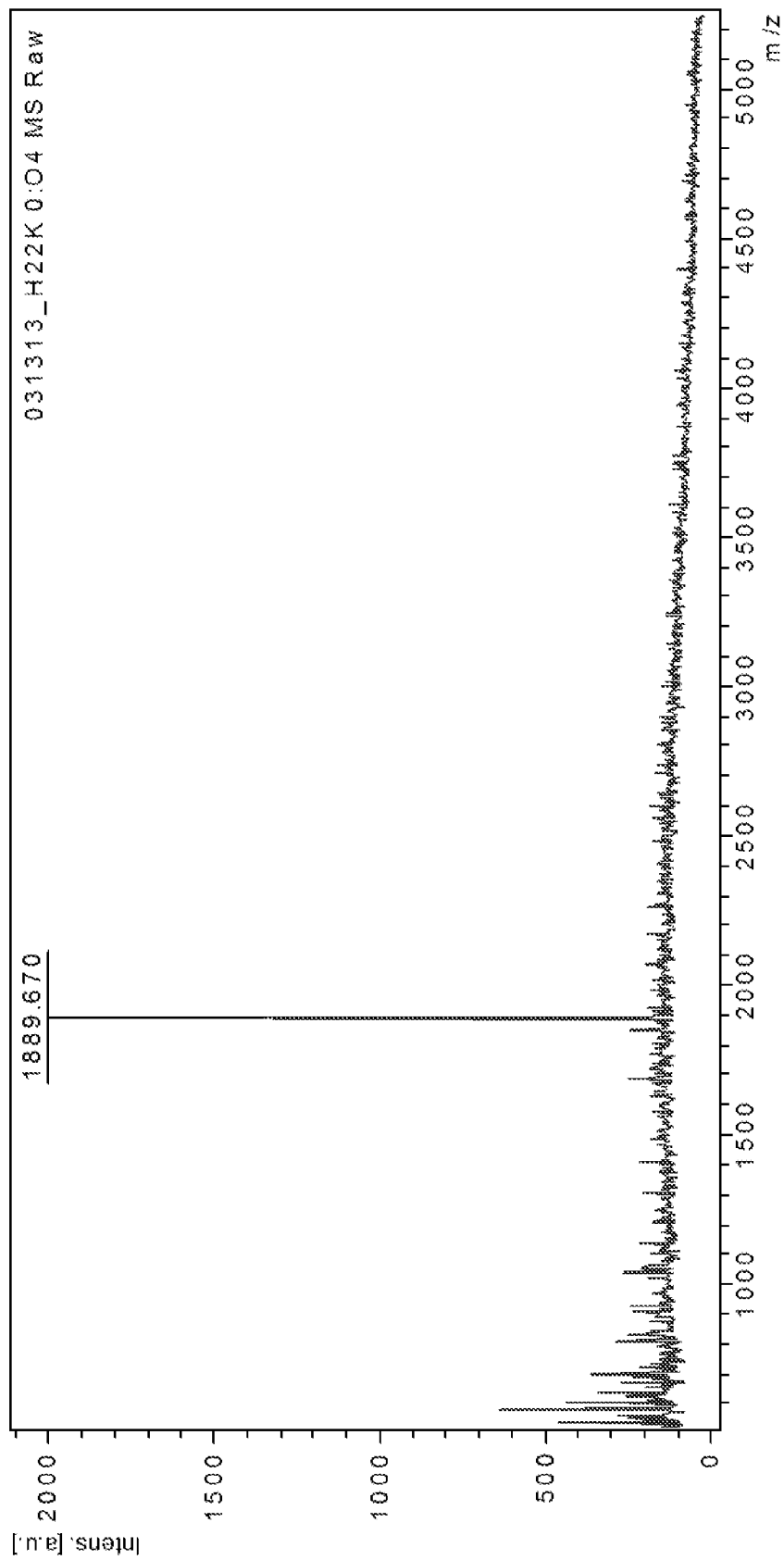
FIG. 2: Reglycosylation of the G0F glycoform using the mutant enzyme β1,4Gal-T1-Y289L and UDP-2-keto-Gal. Transfer of the modified sugar nucleotide was analyzed by mass spectrometry of the modified N-glycans released after PNGase F treatment. The peak at 1889.6 m/z corresponds to the G2F glycoform, indicating that the β-galactosidase-treated m860 IgG1 molecules with a G0F glycoform were fully galactosylated to the G2F glycoform after transfer of the C2-keto-Gal moiety to the terminal GlcNAc residues.

Modification of Degalactosylated m860 Confirmed by MS Analysis of Released Glycans Reglycosylation of the G0F glycoform was accomplished using the mutant enzyme β1,4Gal-T1-Y289L and UDP-2-keto-Gal as the sugar donor. Transfer of the modified sugar nucleotide was analyzed by mass spectrometry of the modified N-glycans released after PNGase F treatment (FIG. 2). A peak at 1889.6 m/z corresponding to the G2F glycoform indicated that the 3-galactosidase-treated m860 IgG1 having a G0F glycoform was fully galactosylated to the G2F glycoform after transfer of the C2-keto-Gal moiety to the terminal GlcNAc residues.

Conjugation of the Small Molecule Drug Auristatin F to m860 IgG1

Figure 3:
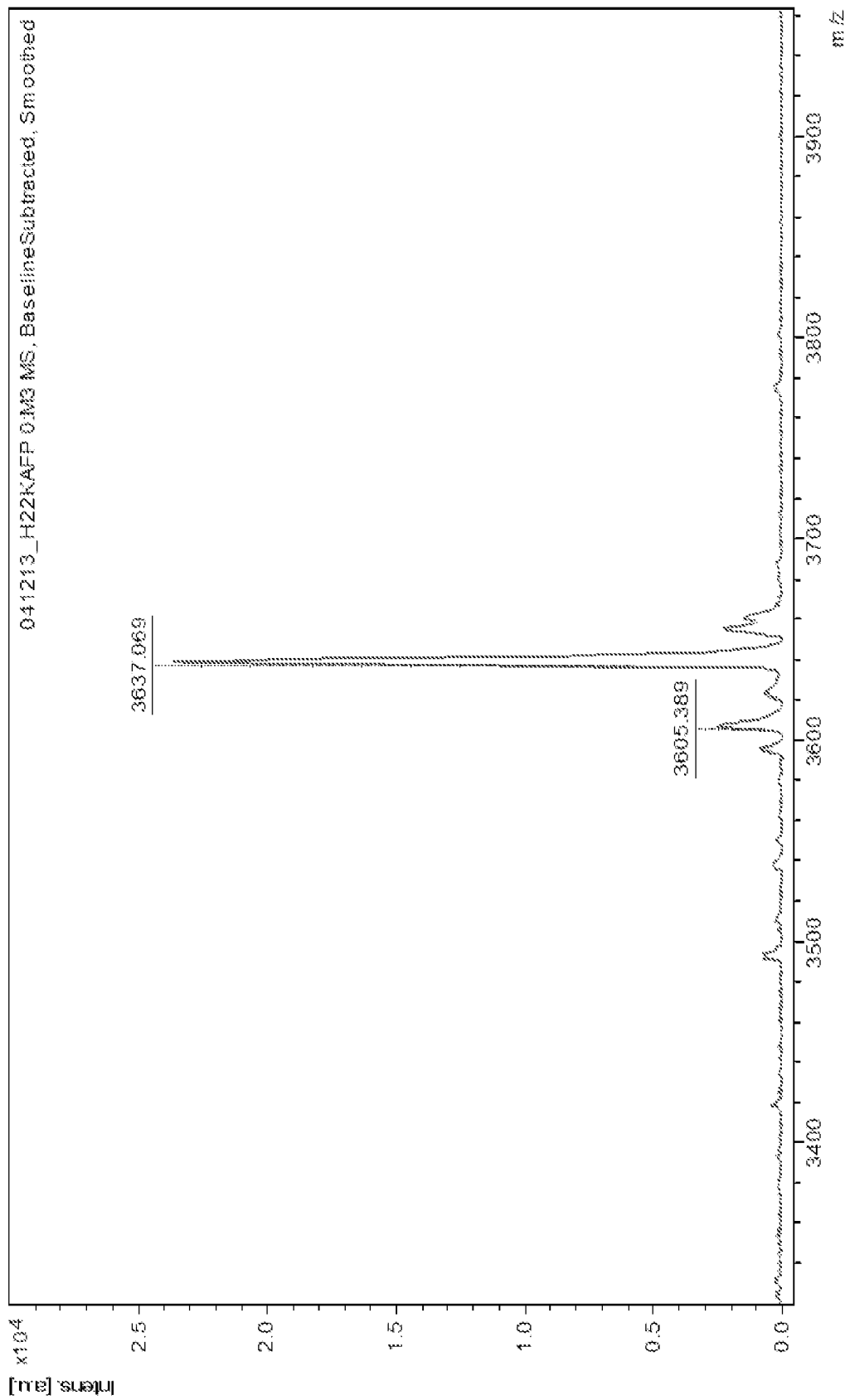
FIG. 3: MALDI/TOF MS analysis of the released glycans through PNGase F treatment of m860 ADC. The peak at 3637 m/z corresponds to nAF (auristatin F with a non-cleavable linker at the C-terminus) conjugated to both arms of N-glycans carrying a C2-keto-Gal in the m860 ADC.

To validate this site-specific antibody drug conjugation, auristatin F (AF) was selected; AF is one of the most commonly used toxins in clinical ADC development. ADCs developed using auristatin F with non-cleavable linker (nAF) at the C-terminus have shown potent cell killing activity and improved pharmacological profile in vivo. The non-cleavable ethylene glycol linker derivatized with an alkoxy-amine was synthesized and attached to the AF as previously described (Axup et al., *Proc Natl Acad Sci USA* 109:16101-16106, 2012). Auristatin F with a non-cleavable linker attached to the C-terminus (nAF) was conjugated to m860 IgG1 through a keto-aminooxy reaction to produce the m860 antibody-drug conjugate (m860 ADC). Conjugation of nAF was confirmed by MS analysis of conjugated glycans released from m860 ADC. Shown in FIG. 3 are the results of MALDI/TOF MS analysis of the glycans released through PNGase F treatment of m860 ADC. The peak at 3637 m/z corresponds to nAF conjugated to both arms of N-glycans carrying a C2-keto-Gal in the m860 ADC. Conjugation of nAF was also confirmed by MS analysis of the conjugated heavy chain.

Figure 4A:
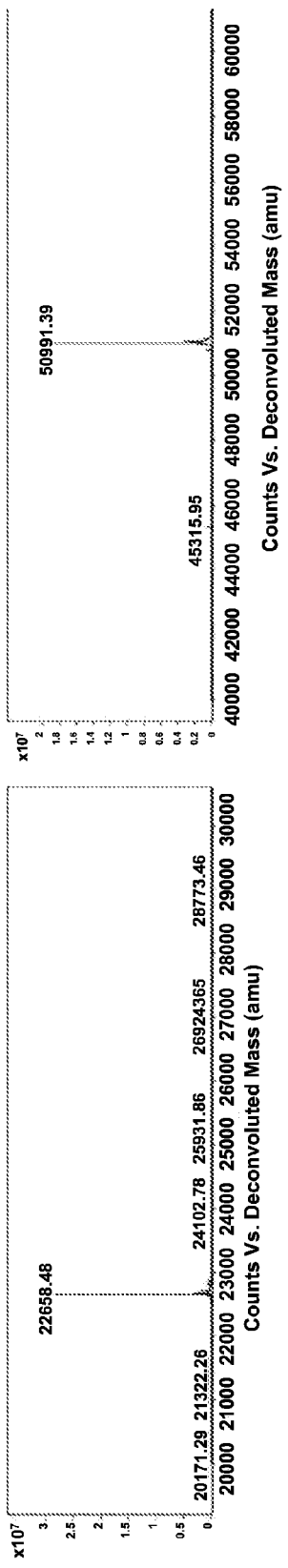
FIGS. 4A-4C: Mass spectrometry analysis of the light chain and heavy chain of IgG1 m860 before (FIG. 4A) and after the keto-modification (FIG. 4B) and after the small molecule drug (nAF) conjugation (FIG. 4C). The molecular weight of the light chains was not impacted after the conjugation. The change in the molecular weight of the heavy chain after modification and subsequent conjugation indicated the efficient conjugation of two small molecule drugs per heavy chain.
Figure 4B:
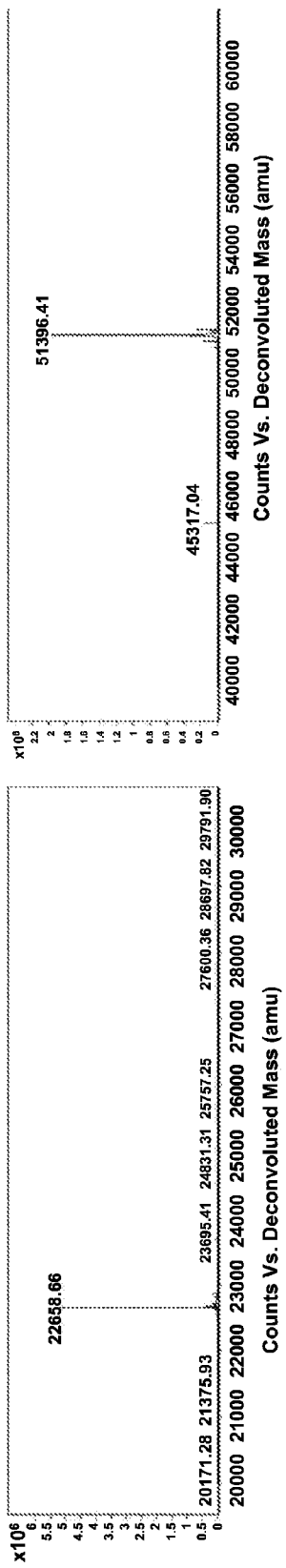
Figure 4C:
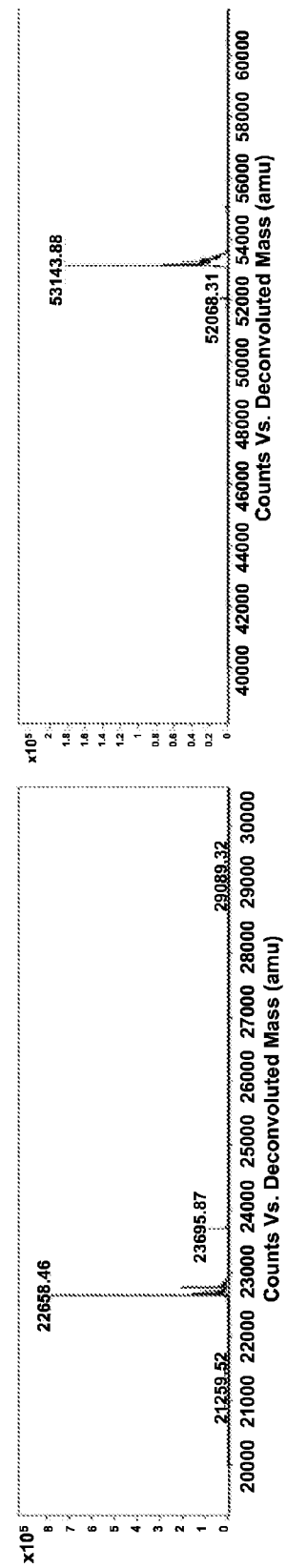

Analysis by ESI-MS revealed that the heavy chain of the antibody drug conjugate has a mass 1747 Da larger than the keto group carrying IgG1 m860 heavy chain, which corresponds to the mass of two nAFs per heavy chain (FIGS. 4A-4C), i.e. an antibody to drug ratio of 1:4. This is also consistent with the MALDI-TOF profile of the released oligosaccharide from the ADC m860 (FIG. 3).

Figure 5:
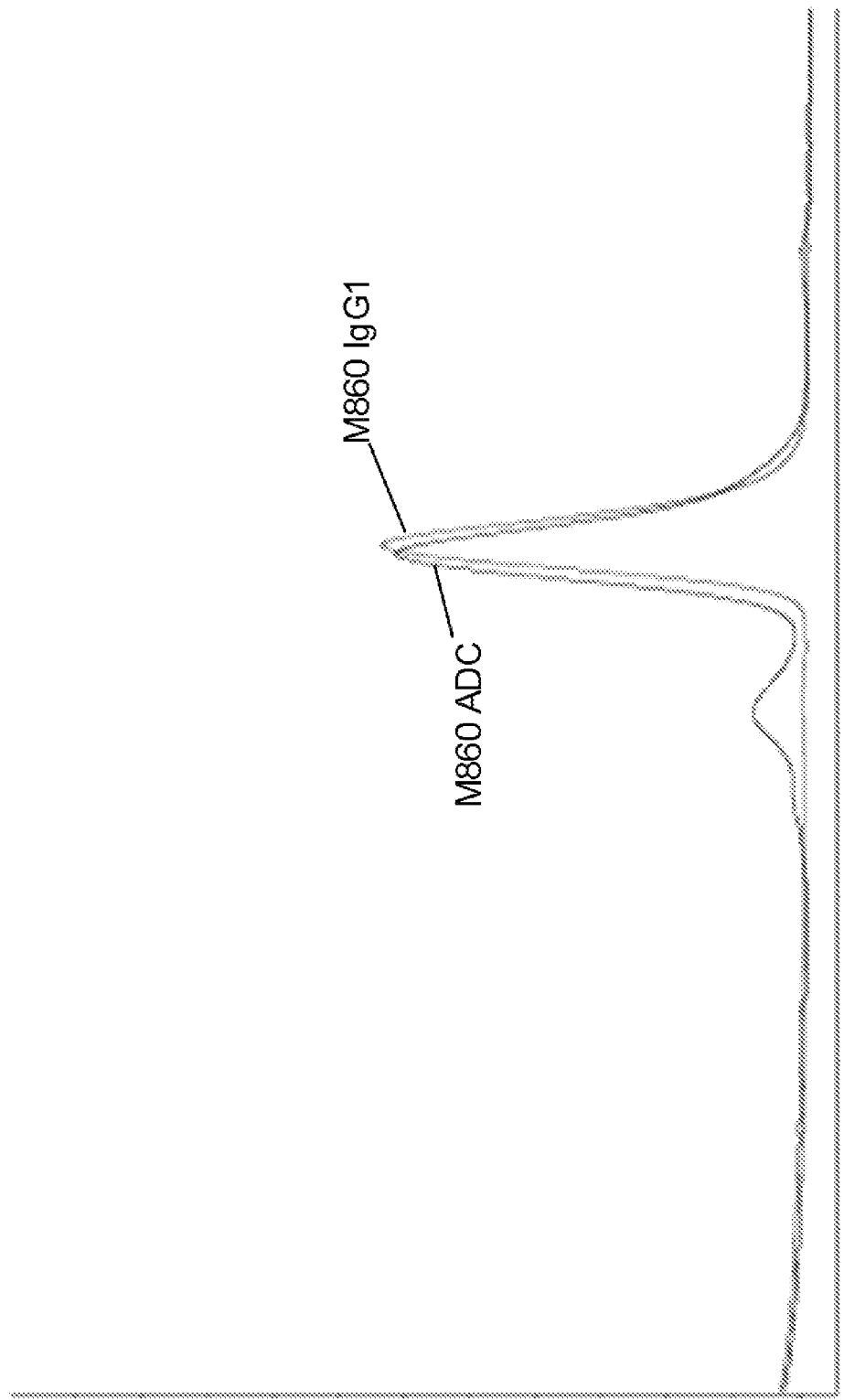
FIG. 5: Size-exclusion chromatography analysis of WT m860 IgG1 and m860 ADC. The major population of the m860 ADC overlapped well with the WT m860 IgG1 profile; about 10% of the preparation exists as oligomer.

Size-exclusion chromatography analysis of the m860 ADC was also performed. The results of size-exclusion chromatography of WT m860 IgG1 and m860 ADC are shown in FIG. 5. The major population of the m860 ADC overlapped well with the WT m860 IgG1 profile; about 10% of the preparation existed as an oligomer.

Binding of m860 IgG1 and m860 ADC

Figure 6A:
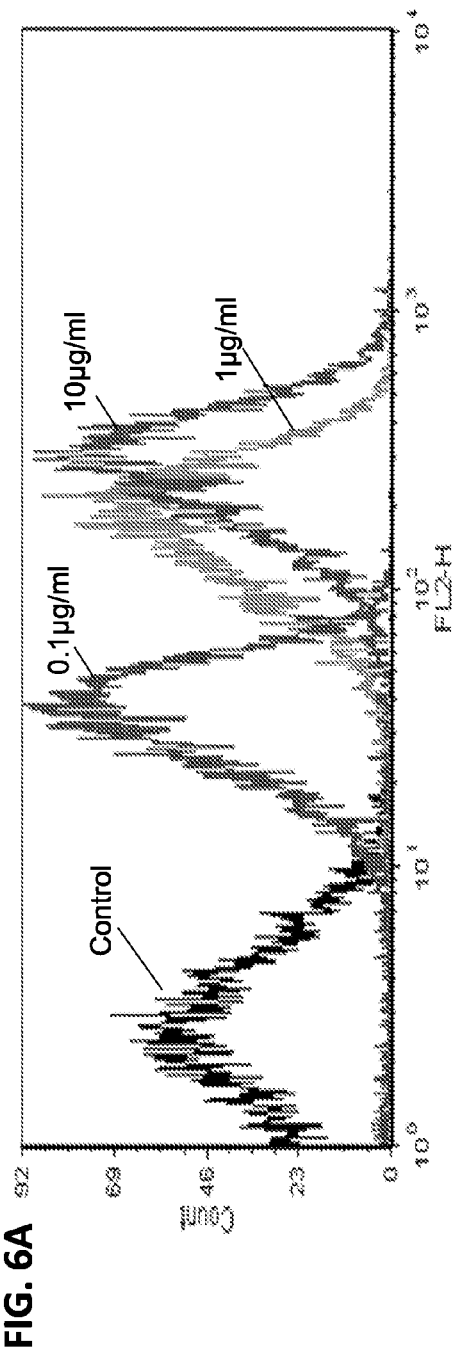
FIGS. 6A-6B: Flow cytometry analysis of the binding of m860 IgG1 before (FIG. 6A) and after (FIG. 6B) drug conjugation. The binding activity of m860 IgG1 to Her2 on SKBR3 was not impacted by nAF conjugation to the N-glycans of the antibody Fc.
Figure 6B:
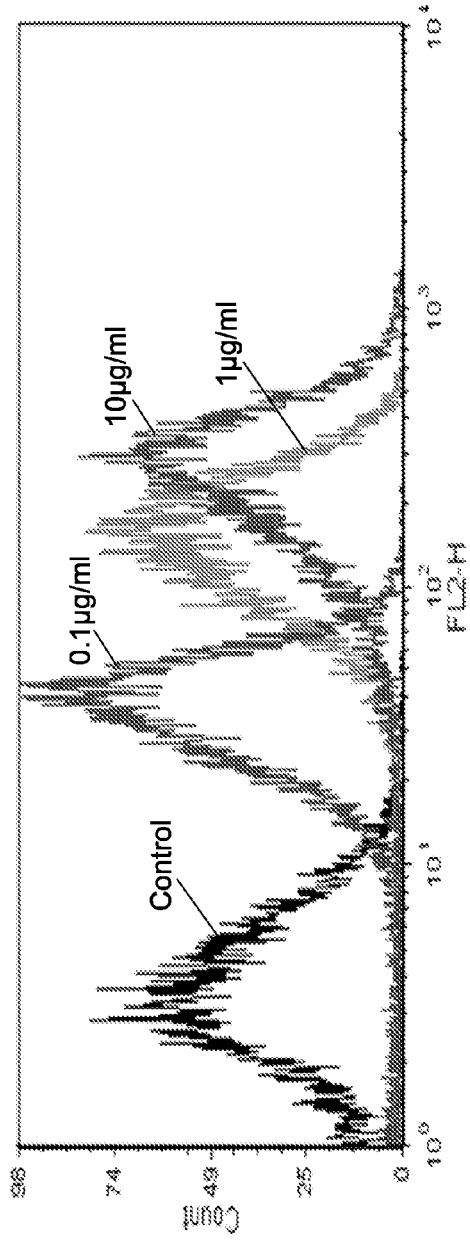

Binding of m860 ADC to Her2-expressing cells, FcγRI (CD64) and FcγRIII (CD16) was evaluated to determine whether conjugation of nAF through glycan engineering altered the binding properties of m860. Flow cytometry analysis was performed to assess binding of m860 IgG1 to Her2-expressing cells before (FIG. 6A) and after (FIG. 6B) drug conjugation. The binding activity of m860 IgG1 to Her2 on SKBR3 cells was not impacted by nAF conjugation to N-glycans of the m860 Fc.

Table 1 and Table 2 summarize the binding properties of m860 ADC to FcγRI and FcγRIII, respectively. Conjugation of nAF to m860 did not alter binding to either FcγRI or FcγRIII.

TABLE 1

Site-specific antibody drug conjugation through N-glycans does not impact the binding of m860 ADC to FcγRI

| Antibody | ka (1/Ms) | kd (1/s) | KD (M) |
| --- | --- | --- | --- |
| M860 IgG1 | 4.479E+4 | 0.001007 | 2.249E−8 |
| M860 IgG1 ADC | 4.362E+4 | 0.001078 | 2.472E−8 |
| Control IgG1 | 7.628E+4 | 0.001372 | 1.798E−8 |

TABLE 2

Site-specific antibody drug conjugation through N-glycans does not impact the binding of m860 ADC to FcγRIII

| Antibody | ka (1/Ms) | kd (1/s) | KD (M) |
| --- | --- | --- | --- |
| M860 IgG1 | 1.108E+4 | 0.01608 | 1.5E−6 |
| M860 IgG1 ADC | 0.925E+4 | 0.01752 | 1.9E−6 |
| Control IgG1 | 2.224E+4 | 0.01484 | 6.7E−7 |

In Vitro Cytotoxicity Assays

Figure 7A:
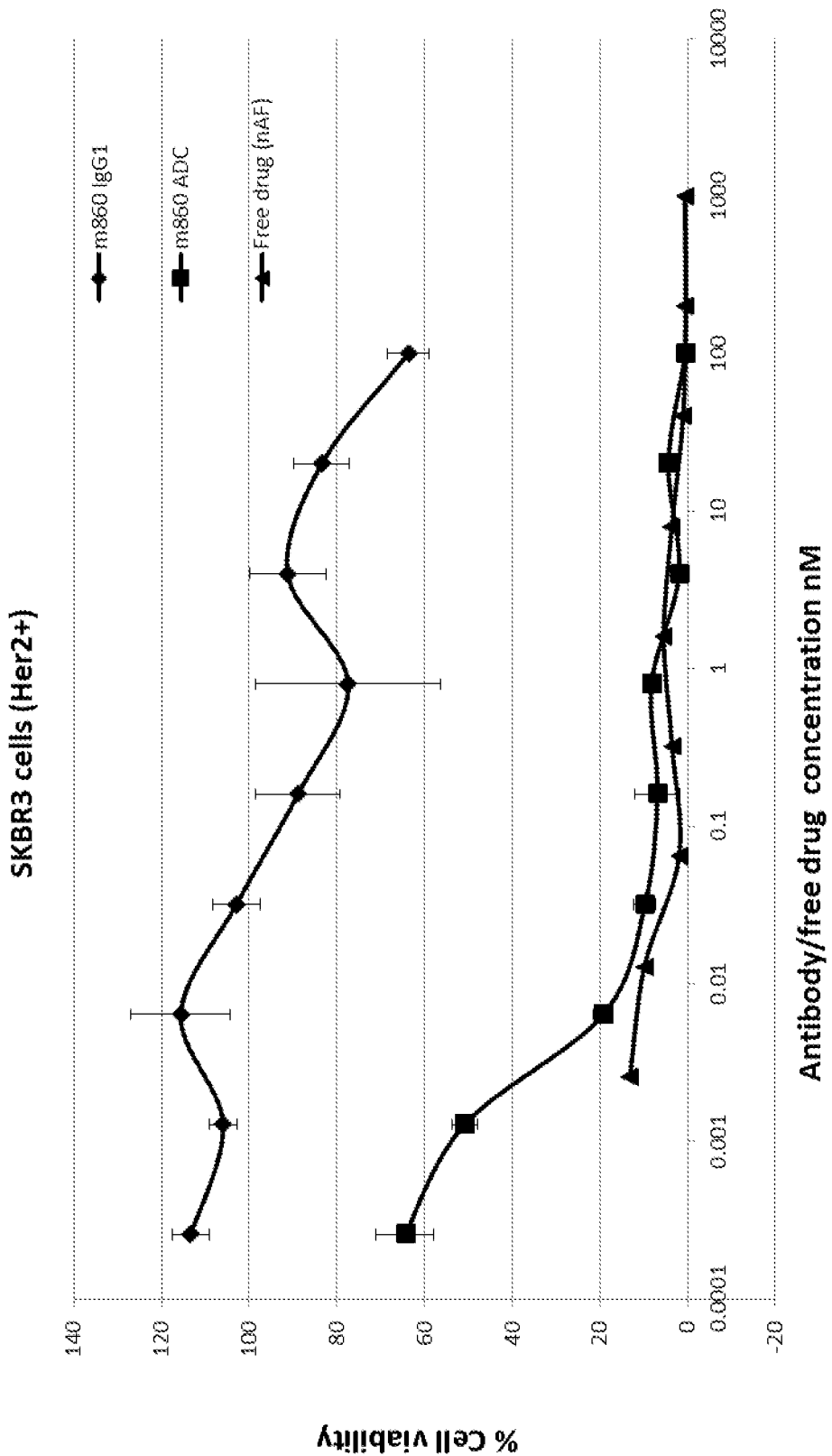
FIG. 7A-7C: In vitro cytotoxicity assays.
Figure 7B:
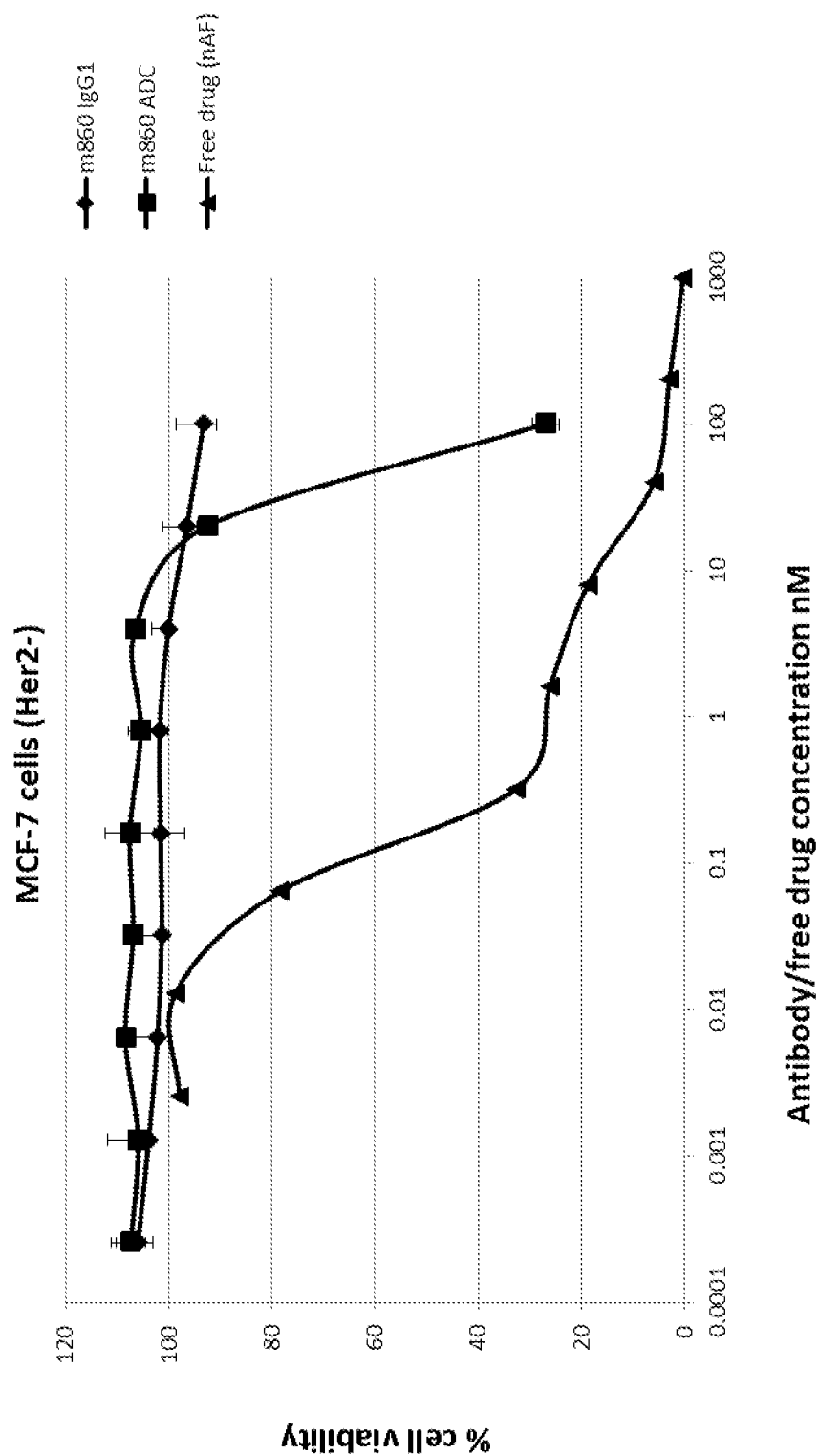
Figure 7C:
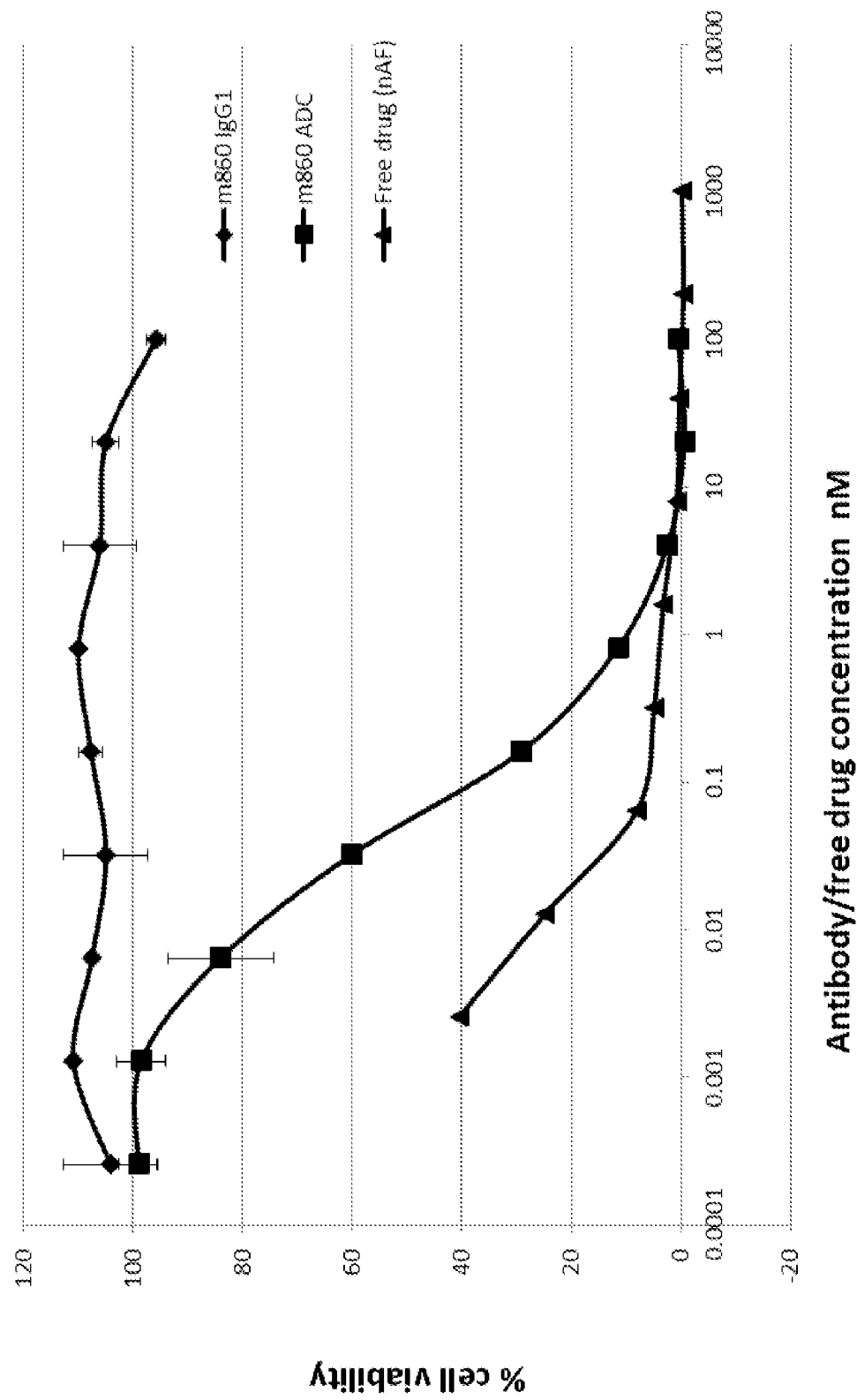

Cytotoxic activity of m860 ADC was tested using cells that overexpress Her2 (SKRB3), cells that do not express Her2 (MCF-7) and cells with moderate Her2 expression (JIMT-1). FIG. 7A shows the results of a cytotoxicity assay of Her-2-overexpressing SKRB3 cells. The m860 ADC was slightly more cytotoxic than free drug (nAF) on SKBR3 cells, while the WT m860 IgG1 did not exhibit any cytotoxicity. FIG. 7B shows the results of a cytotoxicity assay with MCF-7 cells. The m860 ADC was cytotoxic to MCF-7 cells only at a relatively high concentration, while the free drug with linker alone exhibited significant cytotoxicity to MCF-7 cells. The JIMT-1 cell line, which was isolated from a trastuzumab-resistant patient, has moderate Her2 expression compared to SKBR3. The m860 ADC potently killed JIMT-1 cells, while the WT m860 IgG1 alone had little effect on the cells (FIG. 7C). These results demonstrate that m860 ADC is highly cytotoxic and cytotoxicity is specific for Her2-expressing cells.

Example 2: Her2-Specific Monoclonal Antibodies for Detecting Cancer in a Subject or Confirming the Diagnosis of Cancer in a Subject This example describes the use of Her2-specific monoclonal antibodies, such as the m860 antibody disclosed herein, for the detection of cancer in a subject. This example further describes the use of these antibodies to confirm the diagnosis of cancer in a subject.

A blood or tissue sample (such as a biopsy) is obtained from the patient diagnosed with, or suspected of having a Her2-positive cancer (i.e., a cancer that overexpresses Her2, such as breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma or head and neck carcinoma). A sample taken from a patient that does not have cancer can be used as a control. An immunoassay (such as immunohistochemistry or fluorescence in situ hybridization of a tissue sample) is performed to detect the presence of Her2 in the sample (such as Her2-expressing cells in a tissue sample). For example, tissue sections obtained from a patient biopsy and a control tissue sample are contacted with a Her2-specific monoclonal antibody directly conjugated with a detectable label (such as an enzyme) and immunohistochemical detection for Her2 is carried out according to standard procedures (see, for example, Jacobs et al., *J Clin Oncol* 17:1974-1982, 1999; Wang et al., *J Clin Pathol* 53:374-381, 2000). An increase in enzyme activity of the patient sample, relative to the control sample, indicates the anti-Her2 antibody specifically bound proteins from the tissue sample, thus detecting the presence of Her2 protein in the sample. Detection of Her2 protein in the patient sample indicates the patient has a Her2-positive cancer, or confirms diagnosis of cancer in the subject.

Example 3: Her2-Specific ADCs for the Treatment of Cancer

This example describes the use of Her2-specific antibody-drug conjugates for the treatment of cancers that exhibit overexpression of Her2 (referred to herein as a "Her2-positive" cancer), including, but not limited to breast cancer, gastric cancer, esophageal cancer, ovarian cancer, endometrial cancer, stomach cancer, uterine cancer, pancreatic cancer, prostate cancer, bladder cancer, colon cancer, salivary gland carcinoma, renal adenocarcinoma, mammary gland carcinoma, non-small cell lung carcinoma or head and neck carcinoma. Patients diagnosed with a Her2-positive cancer can be treated according to standard procedures in the art (see, for example, Piccart-Gebhart et al., *N Engl J Med* 353:1659-1672, 2005; Romond et al., *N Engl J Med* 353: 1673-1684, 2005; Baselga, *Oncology* 61(suppl 2):14-21, 2001).

In this example, patients diagnosed with Her2-positive breast cancer are administered an ADC comprising a Her2-specific monoclonal antibody (such as m860 disclosed herein) conjugated to the small molecule drug auristatin F. Preparation of the m860 ADC is disclosed herein. In some patients, the ADC is administered by intravenous infusion every three weeks. The dose of ADC administered to a patient varies depending on the weight and gender of the patient, and mode and time course of administration. In some cases, the ADC is administered at a dose of about 1 to about 5 mg/kg. Following treatment, patients are evaluated for cancer progression (including tumor growth and metastasis) and other clinical signs of illness.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated monoclonal antibody that binds Her2, wherein the VH domain of the antibody comprises amino acid residues 26-33, 50-58 and 97-110 of SEQ ID NO: 2 and the VL domain of the antibody comprises amino acid residues 23-34, 52-54 and 91-100 of SEQ ID NO: 4.

2. The isolated monoclonal antibody of claim 1, wherein the amino acid sequence of the VH domain is at least 90% identical to SEQ ID NO: 2; and the amino acid sequence of the VL domain is at least 90% identical to SEQ ID NO: 4.

3. The isolated antibody of claim 1, wherein the amino acid sequence of the VH domain comprises SEQ ID NO: 2; and the amino acid sequence of the VL domain comprises SEQ ID NO: 4.

4. An isolated monoclonal antibody that binds Her2, wherein:
   (i) the VH domain of the antibody comprises SEQ ID NO: 2; and
   (ii) the VL domain of the antibody comprises SEQ ID NO: 4.

5. The monoclonal antibody of claim 1, wherein the antibody is a Fab fragment, a Fab' fragment, a F(ab)'2 fragment, a single chain variable fragment (scFv), or a disulfide stabilized variable fragment (dsFv).

6. The monoclonal antibody of claim 1, wherein the antibody is an IgG.

7. An isolated conjugate comprising the monoclonal antibody of claim 1 and an effector molecule.

8. The isolated conjugate of claim 7, wherein the effector molecule is a drug, toxin or detectable label.

9. The isolated conjugate of claim 8, wherein the drug is a small molecule.

10. The isolated conjugate of claim 8, wherein the drug is auristatin F.

11. The isolated conjugate of claim 8, wherein the toxin is *Pseudomonas* exotoxin or a variant thereof.

12. The isolated conjugate of claim 8, wherein the detectable label is a fluorescence, enzymatic, or radioactive label.

13. An antibody-drug conjugate (ADC) comprising a drug conjugated to a monoclonal antibody that binds Her2, wherein the VH domain of the antibody comprises amino acid residues 26-33, 50-58 and 97-110 of SEQ ID NO: 2 and the VL domain of the antibody comprises amino acid residues 23-34, 52-54 and 91-100 of SEQ ID NO: 4, and wherein the drug is conjugated to an N-glycan of a CH2 domain of the antibody.

14. The ADC of claim 13, wherein the drug is a small molecule.

15. The ADC of claim 13, wherein the drug is an anti-microtubule agent.

16. The ADC of claim 13, wherein the drug is auristatin F.

17. The ADC of claim 16, wherein the auristatin F comprises a non-cleavable linker.

18. The ADC of claim 17, wherein the non-cleavable linker is at the C-terminus of auristatin F.

19. The ADC of claim 13, wherein the antibody to drug ratio is 1:4.

20. The ADC of claim 13, wherein the antibody to drug ratio is 1:2.

21. A composition comprising a therapeutically effective amount of the ADC of claim 13 in a pharmaceutically acceptable carrier.

22. An in vitro method of killing Her2-positive cells, comprising contacting the cells with the ADC of claim 13, thereby killing the Her2-positive cells.

23. A method of detecting a Her2-expressing cell in a biological sample, comprising:
contacting the sample with the monoclonal antibody of claim 1; and
detecting binding of the antibody to the sample,
wherein an increase in binding of the antibody to the sample as compared to binding of the antibody to a control sample detects a Her2-expressing cell in the sample.

24. A method of detecting a Her2-expressing cancer in a subject, comprising:
contacting a sample from a subject diagnosed with cancer with the monoclonal antibody of claim 1; and
detecting binding of the antibody to the sample,
wherein an increase in binding of the antibody to the sample as compared to binding of the antibody to a control sample detects a Her2-expressing cancer in the subject.

25. The method of claim 23, wherein the monoclonal antibody is directly labeled.

26. The method of claim 23, further comprising:
contacting a second antibody that specifically binds the monoclonal antibody with the sample, and
detecting the binding of the second antibody,
wherein an increase in binding of the second antibody to the sample as compared to binding of the second antibody to a control sample detects a Her2-expressing cell in the sample.

27. An isolated nucleic acid molecule encoding the monoclonal antibody of claim 1.

28. The isolated nucleic acid molecule of claim 27, wherein:
(i) the nucleotide sequence encoding the VH domain of the monoclonal antibody comprises SEQ ID NO: 1;
(ii) the nucleotide sequence encoding the VL domain of the monoclonal antibody comprises SEQ ID NO: 3; or
(iii) both (i) and (ii).

29. The isolated nucleic acid molecule of claim 27, operably linked to a promoter.

30. An expression vector comprising the isolated nucleic acid molecule of claim 27.

31. An isolated host cell transformed with the expression vector of claim 30.

32. An isolated monoclonal antibody or antigen-binding fragment thereof that binds Her2, comprising a variable heavy (VH) domain and a variable light (VL) domain wherein:
the VH domain of the antibody comprises the complementarity determining region (CDR) sequences of SEQ ID NO: 2 and the VL domain of the antibody comprises the CDR sequences of SEQ ID NO: 4.

* * * * *